United States Patent
Rosen et al.

(10) Patent No.: US 11,668,021 B2
(45) Date of Patent: Jun. 6, 2023

(54) BASEHIT, A HIGH-THROUGHPUT ASSAY TO IDENTIFY PROTEINS INVOLVED IN HOST-MICROBE INTERACTION

(71) Applicant: YALE UNIVERSITY, New Haven, CT (US)

(72) Inventors: Connor Rosen, New Haven, CT (US); Noah Palm, New Haven, CT (US); Aaron Ring, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 645 days.

(21) Appl. No.: 16/611,952

(22) PCT Filed: May 9, 2018

(86) PCT No.: PCT/US2018/031730
§ 371 (c)(1),
(2) Date: Nov. 8, 2019

(87) PCT Pub. No.: WO2018/208877
PCT Pub. Date: Nov. 15, 2018

(65) Prior Publication Data
US 2021/0079558 A1    Mar. 18, 2021

Related U.S. Application Data

(60) Provisional application No. 62/503,522, filed on May 9, 2017.

(51) Int. Cl.
| C07K 16/12 | (2006.01) |
| C40B 40/02 | (2006.01) |
| C07K 16/42 | (2006.01) |

(52) U.S. Cl.
CPC .............. C40B 40/02 (2013.01); C07K 16/12 (2013.01); C07K 16/1267 (2013.01); C07K 16/1282 (2013.01); C07K 16/4283 (2013.01); C07K 2317/30 (2013.01); C07K 2317/569 (2013.01)

(58) Field of Classification Search
CPC ................ C07K 16/12; C07K 16/1282; C07K 16/1267; C40B 40/02
See application file for complete search history.

(56) References Cited

U.S. PATENT DOCUMENTS

| 2003/0003449 A1 | 1/2003 | Menzel |
| 2004/0265328 A1 | 12/2004 | Robinson |
| 2010/0093563 A1 | 4/2010 | Williamson |
| 2013/0137856 A1 | 5/2013 | Steyaert |

FOREIGN PATENT DOCUMENTS

| WO | 2004093804 A2 | 11/2004 |
| WO | 2009158682 A2 | 12/2009 |
| WO | 2015121092 A1 | 8/2015 |
| WO | 2016077249 A1 | 5/2016 |
| WO | 2017009442 A1 | 1/2017 |

OTHER PUBLICATIONS

Atarashi et al., "Th17 Cell Induction by Adhesion of Microbes to Intestinal Epithelial Cells", Cell, vol. 163, No. 2 (Oct. 8, 2015), pp. 367-380.
Bergstrom et al., "Goblet Cell Derived RELM-β Recruits CD4+T Cells during Infectious Colitis to Promote Protective Intestinal Epithelial Cell Proliferation", PLoS Pathogens, vol. 11, No. 8 (Aug. 18, 2015), Article e1005108.
Blondel et al., "CRISPR/Cas9 Screens Reveal Requirements for Host Cell Sulfation and Fucosylation in Bacterial Type III Secretion System-Mediated Cytotoxicity", Cell Host & Microbe, vol. 20, No. 2 (Aug. 10, 2016), pp. 226-237.
Boder et al., "Yeast surface display for screening combinatorial polypeptide libraries", Nature Biotechnology, vol. 15, No. 6 (Jun. 1997), pp. 553-557.
Feldhaus et al., "Flow-cytometric isolation of human antibodies from a nonimmune Saccharomyces cerevisiae surface display library", Nature Biotechnology, vol. 21, No. 2 (Jan. 21, 2003), pp. 163-170.
Foster et al., "Adhesion, invasion and evasion: the many functions of the surface proteins of Staphylococcus aureus", Nature Reviews Microbiology, vol. 12, No. 1 (2014), pp. 49-62.
Gai et al., "Yeast surface display for protein engineering and characterization", Current Opinion in Structural Biology, vol. 17, No. 4 (2007), pp. 467-473.
Glick et al., "Pathogen receptor discovery with a microfluidic membrane protein array", Proceedings of the National Academy of Science USA, vol. 113, No. 16 (Apr. 19, 2016), pp. 4344-4349.
Hu et al., "Yeast Surface Two-hyprid for Quantitative in Vivo Detection of Protein-Protein Interactions via the Secretory Pathway", Journal of Biological Chemistry, vol. 284, No. 24 (Jun. 12, 2009), pp. 16369-16376.
International Search Report and Written Opinion for PCT/US2018/031730, dated Jul. 30, 2018, 15 Pages.
Ivanov et al.,"Induction of Intestinal Th17 Cells by Segmented Filamentous Bacteria", Cell, vol. 139, No. 3 (Oct. 20, 2009), pp. 485-498.
Javaheri et al., "Heliobacter pylori adhesin HopQ engages in a virulence-enhancing interaction with human CEACAMs", Nature Microbiology, vol. 2 (Oct. 17, 2016), Article 16189.
Jones et al., "Border Control—A Membrane-Linked Interactome of Arabidopsis", Science, vol. 344, No. 6185 (May 16, 2014), pp. 711-716.
Kochut et al., "Bacterial invasion factors: Tools for crossing biological barriers and drug delivery?", European Journal of Pharmaceutics and Biopharmaceutics, vol. 84, No. 2 (Dec. 1, 2012), pp. 242-250.
Koniger et al., "Heliobacter pylori exploits human CEACAMs via HopQ for adherence and translocation of CagA", Nature Microbiology, vol. 2 (Oct. 17, 2016), Article 16188.

(Continued)

Primary Examiner — Jeanette M Lieb
(74) Attorney, Agent, or Firm — Riverside Law LLP

(57) ABSTRACT

The invention provides a BASEHIT screening method for identifying proteins that are involved in host-microbe interactions which may function as therapeutic targets.

9 Claims, 14 Drawing Sheets

Specification includes a Sequence Listing.

(56) References Cited

OTHER PUBLICATIONS

Matrell et al., "A split horseradish peroxidase for the detection of intercellular protein-protein interactions and sensitive visualization of synapses", Nature Biotechnology, vol. 34, No. 7 (Jul. 2016), pp. 774-780.
Muyldermans, "Nanobodies: Natural Single-Domain Antibodies", Annual Reviews Biochemistry, vol. 82, No. 1 (Mar. 13, 2013), pp. 775-797.
Novotny et al., "Intercellular adhesion molecule 1 serves as a primary cognate receptor for the Type IV pilus of nontypeable Haemophilus influenzae", Cell Microbiology, vol. 18, No. 8 (Feb. 26, 2016), pp. 1043-1055.
Okumura et al., "Lypd8 promotes the segregation of flagellated microbiota and colonic epithelia", Nature, vol. 532, No. 7597 (Apr. 7, 2016), pp. 117-121.
Palm et al., "Immunoglobulin A Coating Identifies Colitogenic Bacteria in Inflammatory Bowel Disease", Cell, vol. 158, No. 5 (Aug. 28, 2014), pp. 1000-1010.
Pardon et al., "A general protocol for the generation of Nanobodies for structural biology", Nature Protocols, vol. 9, No. 3 (Feb. 27, 2014), pp. 674-693.
Ruiz et al., "Proteinaceous Molecules Mediating Bifidobacterium-Host Interactions", Fronteirs in Microbiology, vol. 7 (Aug. 3, 2016), Article 1193.
Turroni et al., 2013, "Role of sortase-dependent pili of Bifidobacterium bifidum PRL2010 in modulating bacterium-host interactions." Proc Natl Acad Sci U S A, 110(27):11151-11156.
Vaishnava et al., "The Antibacterial Lectin RegIIIg Promotes the Spatial Segrgation of Microbiota and Host in the Intestine", Science, vol. 334, No. 6053 (Oct. 14, 2011), pp. 255-258.
Wang et al., "A new yeast display vector permitting free scFv amino termini can augment ligand binding affinities", Protein Engineering, Design, & Selection, vol. 18, No. 7 (Jun. 23, 2005), pp. 337-343.
Weiskopf et al., "Engineered SIRPa Variants as Immunotherapeutic Adjuvants to Anticancer Antibodies", Science, vol. 341, No. 6141 (Jul. 5, 2013), pp. 88-91.
Xu et al., "A Distinct Type of Pilus from the Human Microbiom", Cell, vol. 165, No. 3 (Apr. 21, 2016), pp. 690-703.

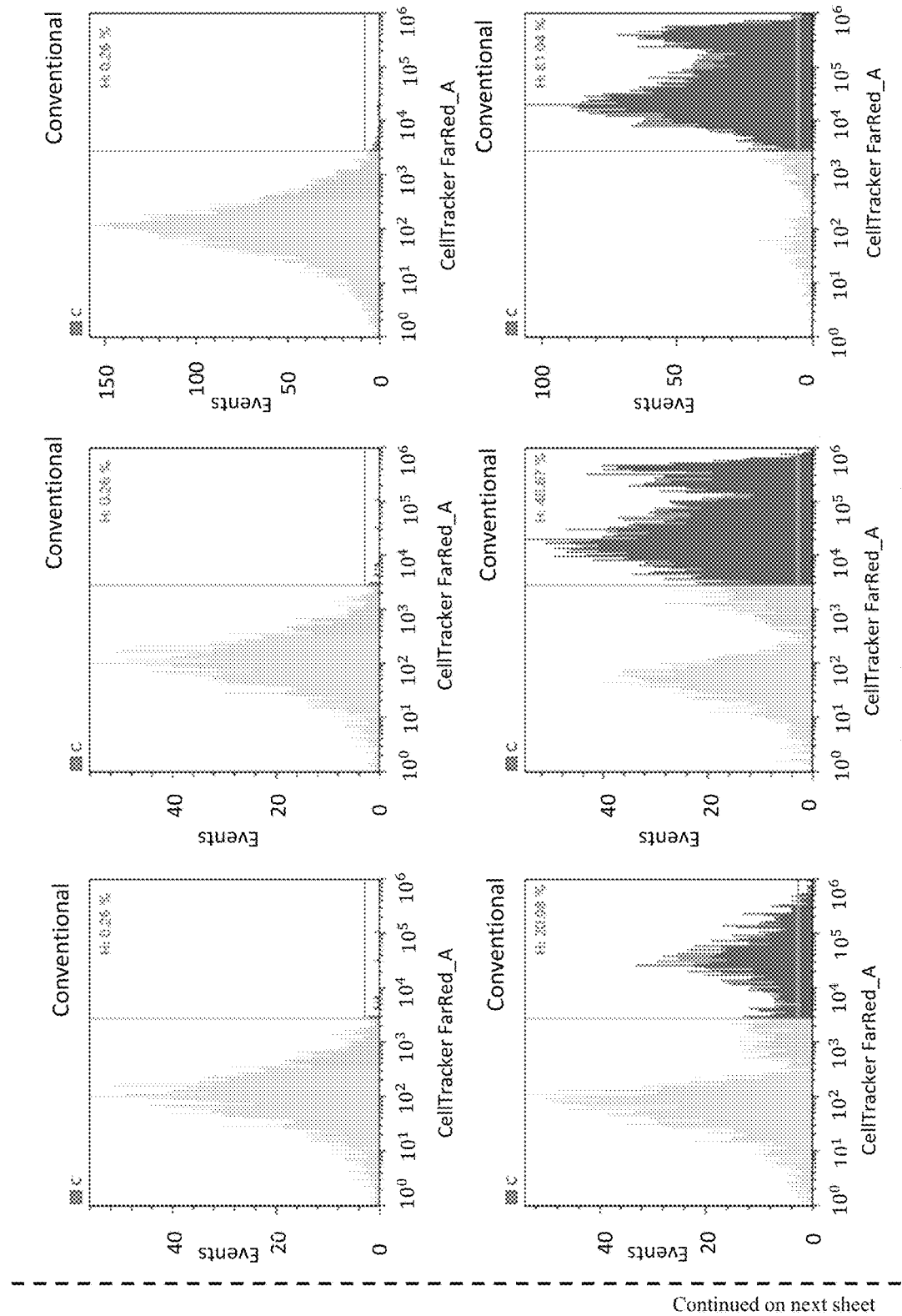
Fig. 2B Continued
Continued on next sheet

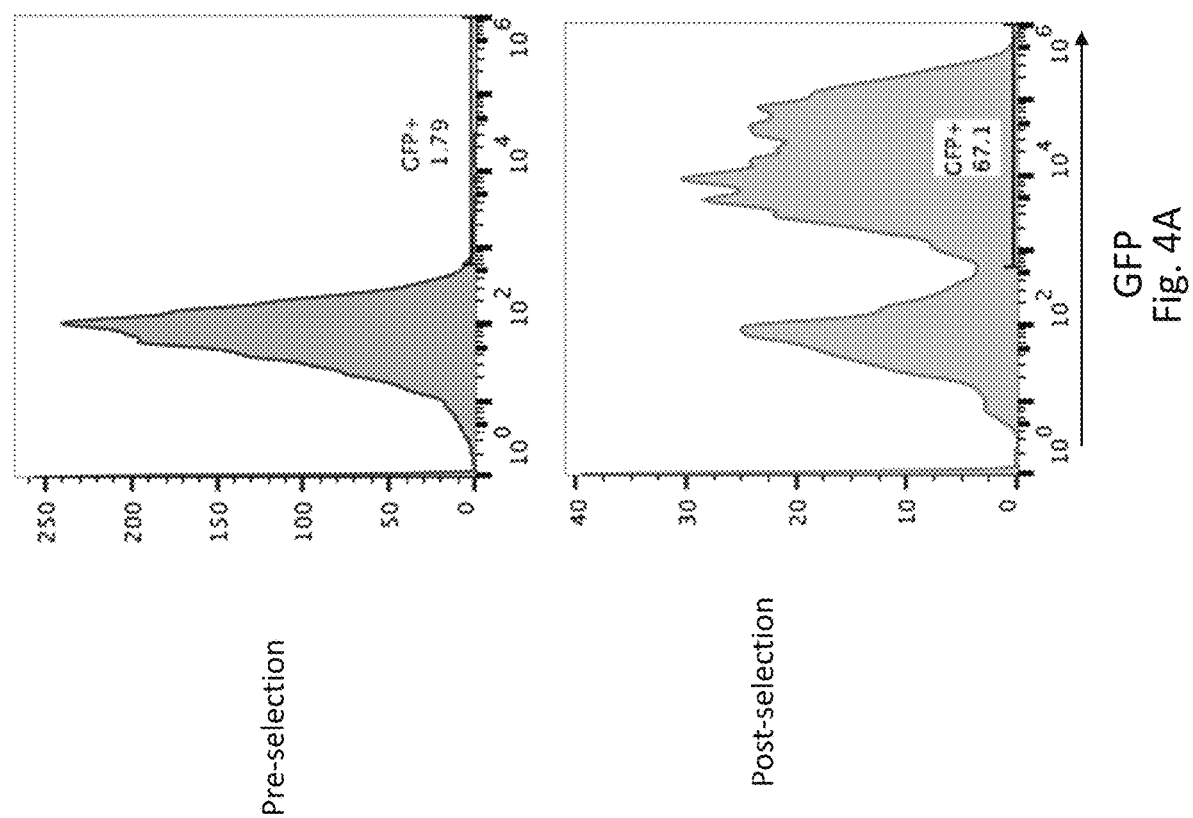

CLUSTAL O(1.2.4) multiple sequence alignment

```
(SEQ ID NO:1)  Nb10   QVQLQESGAA-ACEAGGSLRLSCAASGNISNSVAMGWYRQAPGKERELVAAICYCSSTYYA    59
(SEQ ID NO:2)  Nb5    QVQLQESGGGLVQAGGSLRLSCAASGSISARARMGWYRQA-GKERELVAAISYCATTYYA    59
(SEQ ID NO:3)  Nb8    QVQLQESGGGLVQAGGSLRLSCAASGCTISTSSMGWYRQAPGKEREFVATIADGATTYYA    60
(SEQ ID NO:4)  Nb1    QVQLQESGGGLVQAGGSLRLSCAASGNISRVQAMGWYRQAPGKEREFVAAIDVCATTYYA    60
(SEQ ID NO:5)  Nb3    QVQLQESGGGLVQAGGSLRLSCAASGNISNFTMGWYRQAPGKEREFVAALDVCATTYYA    60
(SEQ ID NO:6)  Nb9    QVQLQESGGGLVQAGGSLRLSCAASGNISQYMGNFTBQAPGKEREFVASIQYCNTNYA    60
(SEQ ID NO:7)  Nb7    QVQLQESGGGLVQAGGSLRLSCAASGNISAYTDMGWYRQAPGKEREFVASIQVGAITYYA    60
(SEQ ID NO:8)  Nb6    QVQLQESGGGLVQAGGSLRLSCAASGTISGDLMGWYRQAPGKEREFVAAIGAGNTNYA    60
(SEQ ID NO:9)  Nb4    QVQLQESGGGLVQAGGSLRLSCAASGSIFGLNAMGWYRQAPGKEREFVAAISACTNTYYA    60
(SEQ ID NO:10) Nb2    QVQLQESGGGLVQAGGSLRLSCAASGSTFRASYMGWYRQAPGKEREFVAAISTGTNTYYA    60
                     ****:****  :*:*:*************:*::    *   *:::**:**::*:; *

Nb10   DSVKGALPLAAKREHRVSADSQ----PE-TGKYRGYLLAG-----LGRSW---LLGPGH    106
               Nb5    DSVKGRFTISRDNAKNTVYLQMNSLKPEDTAVYYCAVQVTFSNP------QSSRLDYWGQGT  114
               Nb8    DSVKGRFTISRDNAKNTVYLQMNSLKPEDTAVYYCAVVQRTTG------RSRVYLNYWGQGT  116
               Nb1    DSVKGRFTISRDNAKNTVYLQMNSLKPEDTAVYYCAVVSKQGH------BRKYYFFYWGQGT  116
               Nb3    DSVKGRFTISRDNAKNTVYLQMNSLKPEDTAVYYCAARSAVTR------TRKYGLYYWGQGT  116
               Nb9    DSVKGRFTISRDNAKNTVYLQMNSLKPEDTAVYYCAAYELIRP-----RBWLYHFYWGQGT  116
               Nb7    DSVKGRFTISRDNAKNTVYLQMNSLKPEDTAVYYCAABWVKRP-----LAFVYLVYWGQGT  116
               Nb6    DSVKGRFTISRDNAKNTVYLQMNSLKPEDTAVYYCAVHHGQTGRFNQVTTRLYNYWGQGT  120
               Nb4    DSVKGRFTISRDNAKNTVYLQMNSLKPEDTAVYYCAVSIPVCTVTRRKGVWTNYWGQGT  120
               Nb2    DSVKGRFTISRDNAKNTVYLQMNSLKPEDTAVYYCAVIE-------YYYQFDYWGQGT    112
                     *****::**:;**: ** *:                      *

Nb10   PGDVSS   112
               Nb5    QVTVSS   120
               Nb8    QVTVSS   122
               Nb1    QVTVSS   122
               Nb3    QVTVSS   122
               Nb9    QVTVSS   122
               Nb7    QVTVSS   122
               Nb6    QVTVSS   126
               Nb4    QVTVSS   126
               Nb2    QVTVSS   118
                     ****
```

Fig. 5

SEQUENCE LISTING

```
<160> NUMBER OF SEQ ID NOS: 10

<210> SEQ ID NO 1
<211> LENGTH: 112
<212> TYPE: PRT
<213> ORGANISM: Artificial Sequence
<220> FEATURE:
<223> OTHER INFORMATION: Chemically Synthesized, Nb10

<400> SEQUENCE: 1

Gln Val Gln Leu Gln Glu Ser Ala Ala Ala Cys Glu Ala Gly Gly Ser
1               5                   10                  15
```

```
Leu Arg Leu Ser Cys Ala Ala Ser Gly Asn Ile Ser Asn Ser Tyr Ala
            20                  25                  30

Met Gly Trp Tyr Arg Gln Ala Pro Gly Lys Glu Arg Glu Leu Val Ala
        35                  40                  45

Ala Ile Gly Tyr Gly Ser Ser Thr Tyr Tyr Ala Asp Ser Val Lys Gly
 50                  55                  60

Ala Leu Pro Leu Ala Ala Lys Arg Glu Lys His Arg Val Ser Ala Asp
 65                  70                  75                  80

Glu Gln Pro Glu Thr Gly Arg Tyr Arg Gly Val Leu Leu Arg Gly Leu
                85                  90                  95

Gly Arg Ser Trp Leu Leu Gly Pro Gly His Pro Gly Asp Val Ser Ser
            100                 105                 110
```

<210> SEQ ID NO 2
<211> LENGTH: 120
<212> TYPE: PRT
<213> ORGANISM: Artificial Sequence
<220> FEATURE:
<223> OTHER INFORMATION: Chemically Synthesized, Nb5

<400> SEQUENCE: 2

```
Gln Val Gln Leu Gln Glu Ser Gly Gly Gly Leu Val Gln Ala Gly Gly
 1               5                   10                  15

Ser Leu Arg Leu Ser Cys Ala Ala Ser Gly Ser Ile Ser Ala Arg Ala
            20                  25                  30

Arg Met Gly Trp Tyr Arg Gln Ala Gly Lys Glu Arg Glu Leu Val Ala
        35                  40                  45

Ala Ile Ser Tyr Gly Ala Thr Thr Tyr Tyr Ala Asp Ser Val Lys Gly
 50                  55                  60

Arg Phe Thr Ile Ser Arg Asp Asn Ala Lys Asn Thr Val Tyr Leu Gln
 65                  70                  75                  80

Met Asn Ser Leu Lys Pro Glu Asp Thr Ala Val Tyr Tyr Cys Ala Val
                85                  90                  95

Gln Val Phe Ser Trp Pro Gln Ser Ser Arg Leu Asp Tyr Trp Gly Gln
            100                 105                 110

Gly Thr Gln Val Thr Val Ser Ser
        115                 120
```

<210> SEQ ID NO 3
<211> LENGTH: 122
<212> TYPE: PRT
<213> ORGANISM: Artificial Sequence
<220> FEATURE:
<223> OTHER INFORMATION: Chemically Synthesized, Nb8

<400> SEQUENCE: 3

```
Gln Val Gln Leu Gln Glu Ser Gly Gly Gly Leu Val Gln Ala Gly Gly
 1               5                   10                  15

Ser Leu Arg Leu Ser Cys Ala Ala Ser Gly Thr Ile Ser Thr Ser Ser
            20                  25                  30

Ser Met Gly Trp Tyr Arg Gln Ala Pro Gly Lys Glu Arg Glu Leu Val
        35                  40                  45

Ala Thr Ile Ala Asp Gly Ala Thr Thr Tyr Tyr Ala Asp Ser Val Lys
 50                  55                  60

Gly Arg Phe Thr Ile Ser Arg Asp Asn Ala Lys Asn Thr Val Tyr Leu
 65                  70                  75                  80
```

Gln Met Asn Ser Leu Lys Pro Glu Asp Thr Ala Val Tyr Tyr Cys Ala
                85                  90                  95

Val Val Gln Arg Thr Thr Gly Arg Ser Arg Val Tyr Leu Asn Tyr Trp
            100                 105                 110

Gly Gln Gly Thr Gln Val Thr Val Ser Ser
            115                 120

<210> SEQ ID NO 4
<211> LENGTH: 122
<212> TYPE: PRT
<213> ORGANISM: Artificial Sequence
<220> FEATURE:
<223> OTHER INFORMATION: Chemically Synthesized, Nb1

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Arg Tyr Gln
            20                  25                  30

Ala Met Gly Trp Tyr Arg Gln Ala Pro Gly Lys Glu Arg Glu Phe Val
            35                  40                  45

Ala Thr Ile Ala Asp Gly Ala Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Val Ser Lys Gln Gly His Arg Arg Lys Tyr Tyr Phe Glu Tyr Trp
            100                 105                 110

Gly Gln Gly Thr Gln Val Thr Val Ser Ser
            115                 120

<210> SEQ ID NO 5
<211> LENGTH: 122
<212> TYPE: PRT
<213> ORGANISM: Artificial Sequence
<220> FEATURE:
<223> OTHER INFORMATION: Chemically Synthesized, Nb3

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ser Asn Trp Tyr
            20                  25                  30

Thr Met Gly Trp Tyr Arg Gln Ala Pro Gly Lys Glu Arg Glu Phe Val
            35                  40                  45

Ala Ala Ile Asp Val Gly Ala Thr Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Arg Phe Ala Val Thr Arg Thr Lys Lys Tyr Gly Leu Tyr Tyr Trp
            100                 105                 110

Gly Gln Gly Thr Gln Val Thr Val Ser Ser
            115                 120

<210> SEQ ID NO 6
<211> LENGTH: 122
<212> TYPE: PRT
<213> ORGANISM: Artificial Sequence
<220> FEATURE:
<223> OTHER INFORMATION: Chemically Synthesized, Nb9

<400> SEQUENCE: 6

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Asn Ile Ser Gln Tyr Val
             20                  25                  30

Gly Met Gly Trp Tyr Arg Gln Ala Pro Gly Lys Glu Arg Glu Phe Val
         35                  40                  45

Ala Ser Ile Gly Tyr Gly Thr Asn Thr Asn Tyr Ala Asp Ser Val Lys
     50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Tyr Glu Leu Ile Arg Pro Arg Arg Trp Leu Tyr His Phe Tyr Trp
            100                 105                 110

Gly Gln Gly Thr Gln Val Thr Val Ser Ser
        115                 120
```

<210> SEQ ID NO 7
<211> LENGTH: 122
<212> TYPE: PRT
<213> ORGANISM: Artificial Sequence
<220> FEATURE:
<223> OTHER INFORMATION: Chemically Synthesized, Nb7

<400> SEQUENCE: 7

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Asn Ile Ser Ala Tyr Tyr
             20                  25                  30

Asp Met Gly Trp Tyr Arg Gln Ala Pro Gly Lys Glu Arg Glu Phe Val
         35                  40                  45

Ala Ser Ile Gly Val Gly Ala Ile Thr Asn Tyr Ala Asp Ser Val Lys
     50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala His Trp Val Lys Arg Pro Leu Ala Phe Val Tyr Leu Val Tyr Trp
            100                 105                 110

Gly Gln Gly Thr Gln Val Thr Val Ser Ser
        115                 120
```

<210> SEQ ID NO 8
<211> LENGTH: 126
<212> TYPE: PRT
<213> ORGANISM: Artificial Sequence
<220> FEATURE:
<223> OTHER INFORMATION: Chemically Synthesized, Nb6

<400> SEQUENCE: 8

```
Gln Val Gln Leu Gln Glu Ser Gly Gly Gly Leu Val Gln Ala Gly Gly
 1               5                  10                  15
```

Ser Leu Arg Leu Ser Cys Ala Ala Ser Gly Thr Ile Ser Gly Asp Leu
            20                  25                  30

Phe Met Gly Trp Tyr Arg Gln Ala Pro Gly Lys Glu Arg Glu Phe Val
            35                  40                  45

Ala Ala Ile Gly Ala Gly Asn Thr Asn Tyr Ala Asp Ser Val Lys
50                      55                  60

Gly Arg Phe Thr Ile Ser Arg Asp Asn Ala Lys Asn Thr Val Tyr Leu
65                      70                  75                  80

Gln Met Asn Ser Leu Lys Pro Glu Asp Thr Ala Val Tyr Tyr Cys Ala
            85                  90                  95

Val His His Gly Gln Thr Gly Arg Phe Asn Gln Val Tyr Phe Arg Leu
            100                 105                 110

Tyr Asn Tyr Trp Gly Gln Gly Thr Gln Val Thr Val Ser Ser
            115                 120                 125

<210> SEQ ID NO 9
<211> LENGTH: 126
<212> TYPE: PRT
<213> ORGANISM: Artificial Sequence
<220> FEATURE:
<223> OTHER INFORMATION: Chemically Synthesized, Nb4

<400> SEQUENCE: 9

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Gly Leu Asn
            20                  25                  30

Ala Met Gly Trp Tyr Arg Gln Ala Pro Gly Lys Glu Arg Glu Phe Val
            35                  40                  45

Ala Ala Ile Ser Ala Gly Thr Asn Thr Tyr Ala Asp Ser Val Lys
50                      55                  60

Gly Arg Phe Thr Ile Ser Arg Asp Asn Ala Lys Asn Thr Val Tyr Leu
65                      70                  75                  80

Gln Met Asn Ser Leu Lys Pro Glu Asp Thr Ala Val Tyr Tyr Cys Ala
            85                  90                  95

Val Ser Ile Pro Val Gly Thr Val Thr Arg Arg Lys Gln Gly Tyr Trp
            100                 105                 110

Phe Asn Tyr Trp Gly Gln Gly Thr Gln Val Thr Val Ser Ser
            115                 120                 125

<210> SEQ ID NO 10
<211> LENGTH: 118
<212> TYPE: PRT
<213> ORGANISM: Artificial Sequence
<220> FEATURE:
<223> OTHER INFORMATION: Chemically Synthesized, Nb2

<400> SEQUENCE: 10

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Arg Ala Ser
            20                  25                  30

Tyr Met Gly Trp Tyr Arg Gln Ala Pro Gly Lys Glu Arg Glu Phe Val
            35                  40                  45

Ala Ala Ile Ser Thr Gly Thr Asn Thr Tyr Tyr Ala Asp Ser Val Lys
50                      55                  60

```
Gly Arg Phe Thr Ile Ser Arg Asp Asn Ala Lys Asn Thr Val Tyr Leu
65                  70              75                  80

Gln Met Asn Ser Leu Lys Pro Glu Asp Thr Ala Val Tyr Tyr Cys Ala
                85              90                  95

Val Ile Glu Tyr Tyr Tyr Tyr Gln Phe Asp Tyr Trp Gly Gln Gly Thr
            100             105                 110

Gln Val Thr Val Ser Ser
        115
```

BASEHIT, A HIGH-THROUGHPUT ASSAY TO IDENTIFY PROTEINS INVOLVED IN HOST-MICROBE INTERACTION

CROSS-REFERENCE TO RELATED APPLICATIONS

This application is a U.S. national phase application filed under 35 U.S.C. § 371 claiming priority to International Patent Application No. PCT/US18/031730, filed May 9, 2018, which is entitled to priority under 35 U.S.C. §119(e) to U.S. Provisional Patent Application No. 62/503,522, filed May 9, 2017, the contents of each of which are incorporated by reference herein in their entireties.

BACKGROUND OF THE INVENTION

Numerous direct cell-cell interactions have been clearly shown to be important for effector functions of well-studied pathogens (Foster et al., 2014, Nat Rev Microbiol, 12(1): 49-62; Ruiz et al., 2016, Front Microbiol, 7:1193; Javaheri et al., 2016, Nat Microbiol, 2:16189; Koniger et al., 2016, Nat Microbiol, 2:16188). For example, it has been shown that direct epithelial adhesion is necessary for the profound immunological effects of Segmented Filamentous Bacteria (SFB), a well-characterized inducer of intestinal Th17 cells (Ivanov et al., 2009, Cell, 139(3): 485-498). In this example, strains derived from different host species that differ in their ability to adhere to the mouse small intestinal epithelium (but which colonize the mouse gut equally well) differ in their Th17-inducing capacity (Atarashi et al., 2015, Cell, 163(2):367-380). SFB is an intensely studied model organism in the microbiota field, but the molecular mechanisms controlling adhesion remain unknown. Other microbes that associate tightly with the host epithelium and associated immune structures are also likely to drive immune maturation, inflammation, and tolerance through direct cell-cell interactions. Similarly, host cells secrete a variety of proteins (most notably IgA, mucins, and antimicrobial peptides) into the lumen of the gut, which can have profound roles in shaping microbial ecology (Okumura et al., 2016, Nature, 532(7597):117-121; Vaishnava et al., 2011, Science, 334 (6053):255-258; Bergstrom et al., 2015, PLoS Pathog, 11(8):e1005108). Identification of the targets of these secreted proteins can provide indications of microbes involved in pathogenesis (Palm et al., 2014, Cell, 158(5): 1000-1010).

It has been difficult to identify extracellular proteins involved in cell-cell contacts, unlike intracellular protein-protein interactions. Recently, several methods have been developed that allow for screens of extracellular protein-protein interactions or proteins involved in cell-cell contacts (Matrell et al., 2016, Nat Biotechnol, 34(7): 774-780; Jones et al., 2014, Science, 344(6185): 711-716; Glick et al., 2016, Proc Natl Acad Sci USA, 113(16): 4344-4349). Each method suffers from limitations which prevent it from being rapidly applied to novel microbiota species. Split-domain proteins, even those which function extracellularly and provide a high degree of sensitivity for protein-protein interactions between cells (Matrell et al., 2016, Nat Biotechnol, 34(7): 774-780) require engineering fusions of specific proteins of interest on each cell. Other methods exist for assessing extracellular or membrane-associated protein-protein interactions (Jones et al., 2014, Science, 344(6185): 711-716; Hu et al., 2009, J Biol Chem, 284(24): 16369-76), but these methods assess only single pairwise protein-protein interactions, missing multi-subunit protein complexes that can be expressed on the surface of microbes for cell-cell interactions (e.g., pili) (Xu et al., 2016, Cell, 165(3): 690-703; Novotny and Bakaletz, 2016, Cell Microbiol, 18(8): 1043-1055; Turroni et al., 2013, Proc Natl Acad Sci USA, 110(27):11151-11156), and require prediction, cloning, and expression of bacterial proteins in a heterologous system, which limits the throughput. The technique that best surpasses these limitations is a recently developed microfluidics-based platform for testing the interaction of fluorescently labeled virions or proteins with an array of in vitro translated membrane proteins (Glick et al., 2016, Proc Natl Acad Sci USA, 113(16): 4344-4349). While this technique was able to identify host proteins recognizing an intact virion, it requires a complex microfluidic setup, and the expression of the host exoproteome was limited (<75% activity for ~2700 host proteins, which represents less than half of the human exoproteome). Additionally, the authors exclusively examine virions or individual proteins, and it is unclear whether larger particles (e.g. bacterial cells) are amenable to use with this technique. A recent report also illustrated the utility of genome-wide CRISPR screens to identify host factors involved in bacterial adhesion and effector function (Blondel et al, 2016, Cell Host Microbe, 20(2): 226-237). However, similar screens may require a co-culture assay to be established, and may be less readily adapted to identifying secreted proteins that bind microbes but mediate difficult-to-detect functions (such as neutralization or exclusion from the mucus layer).

It is of key importance to identify host surface proteins and host secreted proteins that interact with various immunomodulatory members of the microbiota. Because there exists a paucity of high-throughput assays suitable for profiling host-microbe interactions in high throughput, it is necessary to develop a high-throughput assay to identify host proteins that interact with individual microbes. Thus, there is a need in the art for systems and methods for identification of proteins involved in host-microbe interactions to identify potential novel therapeutic targets. The present invention addresses this unmet need in the art.

SUMMARY

In one embodiment, the invention relates to a method of detecting molecules involved in microbial interactions, the method comprising the steps of: a) contacting a first population of cells comprising one or more display molecules with a second population of cells comprising cells from at least one microbial species; b) selecting at least one bound display molecule:microbe complex; and c) detecting the identity of at least one of a bound display molecule.

In one embodiment, the first population of cells comprises a population of yeast cells.

In one embodiment, the display molecule comprises at least one of a protein, a peptide, a fusion protein, an antibody, a nanobody, an affibody, an anticalin, and a monobody.

In one embodiment, the display molecule comprises a nanobody comprising an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10.

In one embodiment, the at least one display molecule comprises a library of host protein sequences.

In one embodiment, the microbial species is a commensal microbe of the host species.

In one embodiment, the microbial species is a pathogenic microbe of the host species.

In one embodiment, the method further comprises identifying the at least one bound display molecule as a therapeutic target.

In one embodiment, the invention relates to a method of detecting a microbe that can interact with at least one target sequence, the method comprising the steps of: a) contacting a first population of cells comprising at least one display molecule comprising at least one target sequence, with a second population of cells comprising cells from at least one microbial species; b) selecting at least one bound display molecule:microbe complex; and c) detecting the identity of the at least one bound microbe.

In one embodiment, the first population of cells comprises a population of yeast cells.

In one embodiment, the display molecule comprises at least one of a protein, a peptide, a fusion protein, an antibody, a nanobody, an affibody, an anticalin, and a monobody.

In one embodiment, the display molecule comprises a nanobody comprising an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10.

In one embodiment, the at least one target sequence comprises a host protein sequence.

In one embodiment, the at least one microbial species is a commensal microbe of the host species.

In one embodiment, the at least one microbial species is a pathogenic microbe of the host species.

In one embodiment, the invention relates to a method of identifying an agent that can affect microbe interaction with at least one target sequence, the method comprising the steps of: a) contacting a first population of cells comprising at least one display molecule comprising at least one target sequence, with a second population of cells comprising cells from at least one microbial species in the presence of an agent; b) evaluating the effect of the candidate agent on microbe interaction with at least one target sequence, wherein the microbial interaction with at least one target sequence is increased or decreased in the presence of the agent; and c) identifying the agent as a mediator of microbe interaction with the at least one target sequence.

In one embodiment, the invention relates to a composition comprising a therapeutic agent targeted to a microbial species, wherein the therapeutic agent comprises a display molecule identified using a method of detecting molecules involved in microbial interactions comprising the steps of: a) contacting a first population of cells comprising at least one display molecule comprising at least one target sequence, with a second population of cells comprising cells from at least one microbial species; b) selecting at least one bound display molecule:microbe complex; and c) detecting the identity of the at least one bound microbe.

In one embodiment, the therapeutic agent comprises an antibody or fragment thereof.

In one embodiment, the agent comprises a bispecific antibody. In one embodiment, the bispecific antibody targets a microbe and a target sequence, wherein the target sequence is selected from the group consisting of an antibody, an antibody fragment and an antibody mimetic. In one embodiment, the bispecific antibody comprises an IgA antibody.

In one embodiment, the therapeutic agent comprises a nanobody. In one embodiment, the nanobody comprises an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10

In one embodiment, the invention relates to a method of treating a disease associated with a microbe comprising administering the therapeutic agent targeted to a microbial species to a subject in need thereof.

In one embodiment, the therapeutic agent comprises an antibody or fragment thereof.

In one embodiment, the agent comprises a bispecific antibody. In one embodiment, the bispecific antibody targets a microbe and a target sequence, wherein the target sequence is selected from the group consisting of an antibody, an antibody fragment and an antibody mimetic. In one embodiment, the bispecific antibody comprises an IgA antibody.

In one embodiment, the therapeutic agent comprises a nanobody. In one embodiment, the nanobody comprises an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10.

In one embodiment, the invention relates to a composition comprising a nanobody. In one embodiment, the nanobody comprises an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the illustrative exemplary embodiments shown in the drawings.

FIG. 2, comprising

FIG. 2A depicts an outline of exemplary selection conditions. Rounds 1 and 2 were performed by magnetic counter-selection against the IgA negative community followed by positive magnetic selection for Ery128 binding. Rounds 3 and 4 were performed by FACS with negative selection against IgA-community binding and positive selection with Ery128 binding, switching the fluorophores between rounds. FIG. 2B depicts results of exemplary experiments, providing a summary of all selection rounds, as measured by flow cytometry. Yeast from each round of selection were stained with either biotinylated IgA negative community bacteria, or biotinylated Ery128, followed by a fluorescent streptavidin secondary.

FIG. 4, comprising FIG. 4A through FIG. 4D, depicts exemplary experimental results demonstrating the BASEHIT proof-of-principle. FIG. 4A depicts exemplary experimental results demonstrating enrichment of IgG1-Fc displaying GFP+ yeast after one round of selection with *Staphylococcus aureus* expressing Protein A. FIG. 4B depicts exemplary experimental results demonstrating pre- and post-selection binding of yeast displaying nanobodies selected from a 500-million-member library. Nanobodies were selected negatively against binding to control IgA-community bacteria (top panels) and positively for binding to *Erysipelotrichaceae* sp. (Ery128, bottom panels). Binding of the yeast pool after four rounds of MACS and FACS selections is shown. FIG. 4C depicts exemplary experimental results demonstrating specificity of a single representative nanobody isolated from the pool shown in FIG. 4B for Ery128. Grey histograms represent control stained bacteria (IgA-community control bacteria, top panel, or Ery128, bottom panel), and red histograms represent staining with the nanobody NB10. FIG. 4D depicts exemplary experimental results demonstrating staining of individual nanobodies from the pool shown in FIG. 4B. IgA-community (pink) or Ery128 (orange) cultures were stained with recombinant nanobody-Fc fusion and staining was calculated as MFI.

FIG. 5 depicts the protein sequences of the nanobodies targeting Ery128 isolated through the described selections.

FIG. 6, comprising FIG. 6A depicts staining of fecal bacteria demonstrating specificity of Nb10. Fecal bacteria from mice colonized with the IgA-community or the IgA-community together with Ery128 were stained with Nb10 and a fluorescent secondary antibody, and detected via flow cytometry. The gated population ("Nanobody+") represent bacteria that are bound by the recombinant nanobody. FIG. 6B depicts the gating strategy for FACS sorting of fecal bacteria from a mouse colonized with IgA-community and Ery128. Fecal bacteria were stained with Nb10 and fluorescent secondary antibody as in FIG. 6A, and the two populations that were bound ("D") or not ("C") by the nanobody were sorted and subjected to 16s rRNA sequencing. FIG. 6C depicts the sequencing results from the sorting experiment in FIG. 6B. Each species detected was normalized to representation in the nanobody-bound population by dividing by representation in the nanobody-unbound population to show specific enrichment by nanobody staining and sorting.

DETAILED DESCRIPTION

Figure 1:
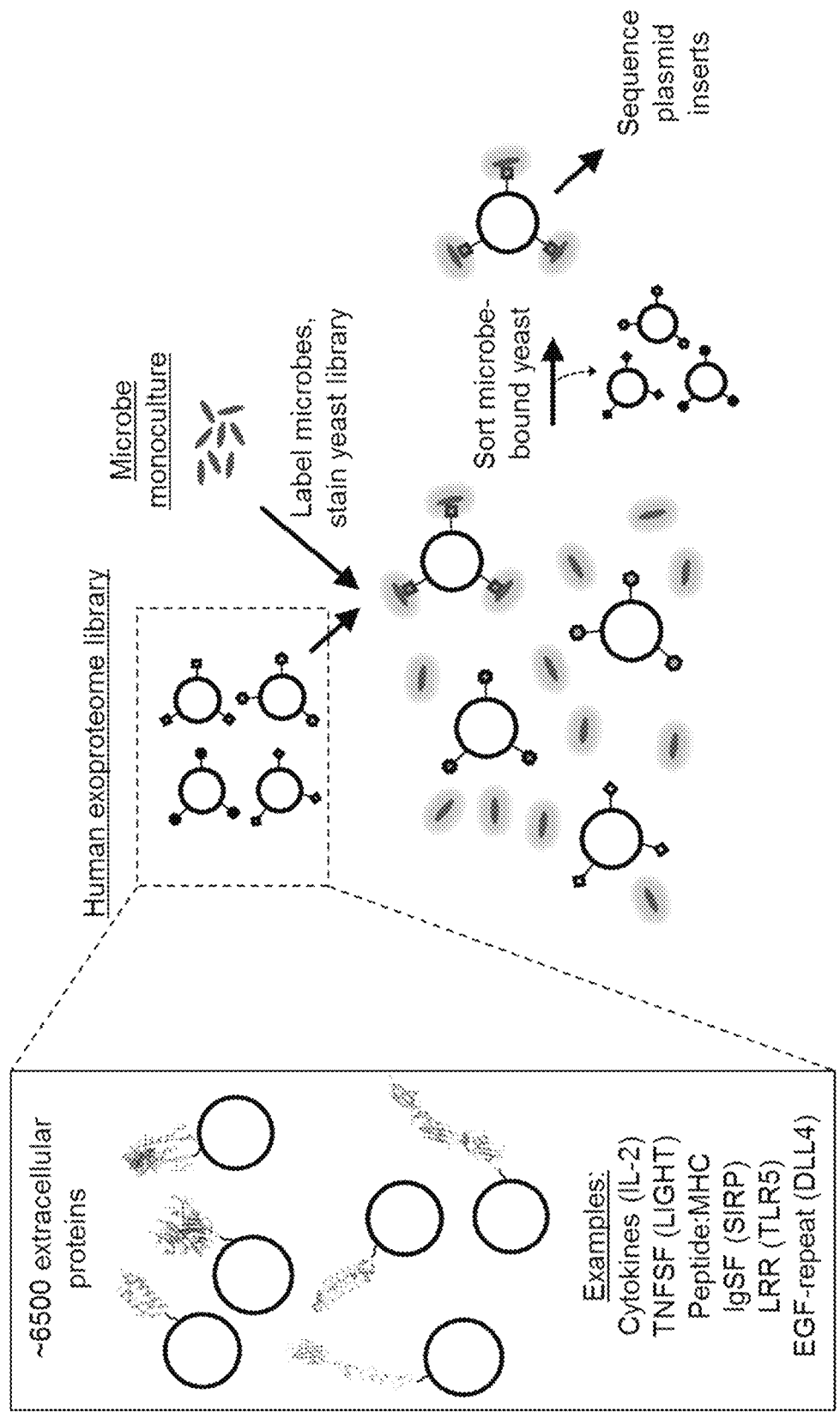
FIG. 1 depicts a schematic diagram of the BASEHIT experimental outline. Microbes isolated in monoculture are labeled (e.g., fluorescently or with biotin) and used to stain a yeast pool displaying a library of host extracellular proteins. The yeast can then be sorted based on their binding of the microbes and the plasmids encoding microbe-binding proteins can be sequenced.

The present invention relates to systems, methods and compositions for identifying proteins involved in host-microbe interactions. In one embodiment, a host-microbe interaction is an interaction between a cell surface protein of a cell of a host organism and a microbe. In one embodiment, a host-microbe interaction is an interaction between a secreted protein of a cell of a host organism and a microbe. In one embodiment, a microbe is a pathogenic organism. In one embodiment, a microbe is considered a commensal organism of the host. Therefore, in various embodiments a protein involved in the interaction serves as a therapeutic target for either increasing or decreasing host-microbe interaction.

In various embodiments a host organism comprises any animal including, but not limited to, an avian (e.g., poultry, e.g., chicken), a mammal (e.g., cat, dog, mouse, primate or human), and/or an agricultural animal (e.g., pig, horse, cow, or sheep.)

The present invention relates generally to a method of screening for at least one protein that participates in a host-microbe interaction, the method comprising: contacting a first population of cells comprising a display library with a second population of microbial cells and detecting binding between a display molecule and a microbial cell.

In one embodiment, the display library contains cells expressing at least about 1, 2, 10, 100, 1,000, 10,000, 100,000, 200,000, 400,000, 1 million, or more than 1 million amino acid sequences. In one embodiment, the at least about 1, 2, 10, 100, 1,000, 10,000, 100,000, 200,000, 400,000, 1 million, or more than 1 million amino acid sequences are each displayed on the surface of at least one cell in a display library. In one embodiment the amino acid sequences comprise proteins, peptides, antibodies, single-domain antibody-like molecules, fragments thereof, or combinations thereof. In one embodiment, at least one amino acid sequence comprises less than about 500, 400, 300, 200, 100, 90, 80, 70, 60, 50, 40, 30 or less than 20 amino acid residues. In one embodiment, at least one amino acid sequence comprises more than about 20, 30, 40, 50, 60, 70, 80, 90, 100, 200, 300, 400, or more than 500 amino acid residues.

In certain embodiments, the amino acid sequences for display in a display library of the invention are representative of the proteome of a species. In various embodiments, the amino acid sequences for display in a display library of the invention may be representative of all or a portion of the proteins expressed in a specific cell type (e.g., expressed in a gut epithelial cell), may be cell surface proteins or fragments thereof, may be secreted proteins or fragments thereof, may be randomly generated peptides, or may be a library of artificially generated antibodies, antibody-like molecules, or antibody mimetics (e.g., nanobodies, affibodies, anticalins, monobodies).

In one embodiment, the method comprises contacting a display library expressing a plurality of distinct amino acid sequences with a plurality of bacterial cells from a single pure bacterial culture. Such an embodiment may find use in identifying amino acid sequences that are involved in interactions with the single bacterial species.

In one embodiment, the method comprises contacting a display library expressing a single amino acid sequence with a plurality of bacterial cells from a mixed or from multiple bacterial cultures. Such an embodiment is useful for identifying bacterial species that are involved in interactions with the single amino acid sequence.

In one embodiment, a mixed bacterial culture may comprise more than about 1, 2, 3, 4, 5, 6, 7, 8, 9, 10, 15, 20, 25, 30, 40, 50 or more than about 50 different bacterial species. In one embodiment, the more than about 1, 2, 3, 4, 5, 6, 7, 8, 9, 10, 15, 20, 25, 30, 40, 50 or more than about 50 different bacterial species are from a single phylum. In one embodiment, the more than about 1, 2, 3, 4, 5, 6, 7, 8, 9, 10, 15, 20, 25, 30, 40, 50 or more than about 50 different bacterial species are from multiple phyla. In one embodiment, the more than about 1, 2, 3, 4, 5, 6, 7, 8, 9, 10, 15, 20, 25, 30, 40, 50 or more than about 50 different bacterial species are gram positive, gram negative, or a combination thereof.

In one embodiment, at least one of the cells for use in the method of the invention are labeled. In one embodiment, the method comprises the use of a labeled bacterial population. In one embodiment, the method comprises the use of a labeled yeast population. For example, in an embodiment wherein the bacterial population is a single pure bacterial culture, the bacterial population may be labeled. As an additional example, in an embodiment wherein the display library expresses a single amino acid sequence, the yeast population may be labeled. Exemplary labeling methods for use in the method of the invention include, but are not limited to, chemical labeling (e.g., cell-surface biotinylation, etc.), fluorescent labeling (e.g., through endogenously expressed fluorescent proteins or addition of chemically-reactive fluorescent dyes such as carboxyfluorescein succinimidyl ester (CFSE) or N-Hydroxysuccinimide (NHS)-fluorescein, etc.), or other common specific labeling techniques (including, for example, expression of an epitope tag selectively recognized by an antibody).

In one embodiment, the method of screening for one or more proteins that participate in cell-cell interactions further comprises isolating a labeled cell bound to an interacting partner. In one embodiment, the method comprises isolating a bacterial cell bound to a yeast cell. Exemplary isolation methods include, but are not limited to, magnetic (MACS) or fluorescent (FACS) cell sorting, affinity purification of cells, centrifugation and differential sedimentation. In any isolation procedure, it is expected that cells that bind the labeled cells of the invention will be isolated in parallel, permitting their subsequent identification.

In one embodiment, the method of screening for one or more proteins that participate in cell-cell interactions further comprises using sequencing to identify a cell or protein that bound to a labeled cell of the invention. In one embodiment, the sequencing comprises sequencing of a nucleic acid molecule encoding a protein that is expressed in a yeast cell. In one embodiment, the sequencing comprises exome sequencing, whole genome sequencing, or 16S rRNA sequencing of a bacterial cell. In various embodiments, sequencing may be done through isolation of individual clones and Sanger sequencing, or through high-throughput next-generation sequencing techniques.

In one embodiment, the present invention provides a method of identifying an agent that interferes with cell-cell interactions. Therefore, in one embodiment, the method is performed in the presence of an agent or library of test agents. In one embodiment, the test agent is an antibacterial agent, a small molecule, a peptide, an antibody, a nucleic acid molecule or a pharmaceutical agent.

In one embodiment, the present invention provides a method of identifying a therapeutic target, the method comprising: performing any of the foregoing methods, thereby identifying one or more protein involved in host-microbe interaction, and identifying the one or more protein involved in host-microbe interaction as a therapeutic target.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

As used herein the term "cell surface molecule" refers to a peptide, polypeptide, binding domain, ligand, lipid, or carbohydrate that is directed to the extracellular surface of the host cell. The cell surface molecule may be anchored to the cell surface by covalent binding or non-covalent binding. The cell surface molecule may include a phospholipid, carbohydrate, or protein through which it attaches to the surface of the host cell. The cell surface molecule may be a polypeptide that binds to, or is conjugated to, a phospholipid, carbohydrate, or a polypeptide on the surface of the cell. For example, the polypeptide may use a phosphatidyl-inositol-glycan (GPI) anchor to attach to the surface of the cell, such as a-agglutinins, α-agglutinins, and flocculins. The cell surface molecule may also be a transmembrane protein.

"Coding sequence" or "encoding nucleic acid" as used herein may refer to the nucleic acid (RNA or DNA molecule) that comprise a nucleotide sequence which encodes an antigen set forth herein. The coding sequence may further include initiation and termination signals operably linked to regulatory elements including a promoter and polyadenylation signal capable of directing expression in the one or more cells of an individual or mammal to whom the nucleic acid is administered. The coding sequence may further include sequences that encode signal peptides.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease, or disorder, the frequency with which such a sign or symptom is experienced by a patient, or both, is reduced.

As used herein the term "display molecule" refers to a molecule that can be localized to the surface of a target cell. The display molecule will typically comprise a first amino acid sequence to be displayed (e.g., a protein of interest, etc.) and a second amino acid sequence that anchors the display molecule to the surface of the target cell (e.g., a transmembrane domain, etc.). In certain instances the first and second amino acid sequences are linked in a single polypeptide. In an alternative embodiment, the first and second amino acid sequences may interact with each other to anchor the first amino acid sequence to the surface of a target cell. A display molecule may comprise a peptide, polypeptide, binding domain, ligand, lipid, or carbohydrate or combination thereof. The display molecule may also comprise a tag or peptide that can be labeled so as to detect binding of the display molecule to the cell surface, or sort cells displaying said molecule.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "gene" means the segment of DNA involved in producing a polypeptide chain. It may include regions preceding and following the coding region (leader and trailer) as well as intervening sequences (introns) between individual coding segments (exons).

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein the term "display library" refers to a plurality of cells, wherein each cell comprises a non-identical display molecule that is displayed on the surface of the cell.

"Measuring" or "measurement," or alternatively "detecting" or "detection," means assessing the presence, absence, quantity or amount (which can be an effective amount) of a given substance.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al, Mol. Cell. Probes 8:91-98 (1994)). The term nucleic acid is used interchangeably with gene, cDNA, and mRNA encoded by a gene.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

As used herein, a "plurality of cells" herein is meant roughly from about $10^3$ cells to $10^8$ or $10^9$, with from $10^6$ to $10^8$ being common.

As used herein, the term "plurality of display molecules" refers to at least two copies of a display molecule displayed on the surface of a target cell. In certain instances, each unique display molecule is displayed by a different target cell.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the promoters from GAL1 (galactose), PGK (phosphoglycerate kinase), ADH (alcohol dehydrogenase), AOX1 (alcohol oxidase), HIS4 (histidinol dehydrogenase), metallothionein, 3-phosphoglycerate kinase, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

A "reporter gene" encodes proteins that are readily detectable due to their biochemical characteristics, such as enzymatic activity or chemifluorescent features. One specific example of such a reporter is green fluorescent protein. Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282: 864-869); luciferase (lux); β-galactosidase; LacZ; β-glucuronidase; and alkaline phosphatase (Toh, et al. (1980) Eur. J. Biochem. 182: 231-238; and Hall et al. (1983) J. Mol. Appl. Gen. 2: 101), each of which are incorporated by reference herein in its entirety. Other suitable reporters include those that encode for a particular epitope that can be detected with a labeled antibody that specifically recognizes the epitope.

As used herein, the term "subject" refers to a host organism, for example, a human or another mammal (e.g., primate, dog, cat, goat, horse, pig, mouse, rat, rabbit, and the like.). In many embodiments of the present invention, the subject is a human being. In such embodiments, the subject may be referred to as an "individual" or a "patient."

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The systems, methods and compositions are based on a screening method that employs a display library of expressed and/or secreted proteins of a host organism for use in detecting proteins involved in host-microbe interaction. The screening method is referred to herein as the BASEHIT method.

Consequently, described herein are display libraries and methods of using the libraries to probe for microbial interactions. In one embodiment, the library displays at least about 1, 2, 10, 100, 1,000, 10,000, 100,000, 200,000, 400,000, or 1 million or more amino acid sequences.

Compositions

Described herein are compositions useful as components of a BASEHIT screening system for identifying proteins involved in host-microbe interaction. The components can be used in a screen to identify therapeutic targets that can modulate a host-microbe interaction, and for therapeutic or pharmaceutical agent identification or development.

The library proteins of the present invention are produced by culturing a cell transformed with nucleic acid, such as an expression vector, containing nucleic acid encoding a library protein, under the appropriate conditions to induce or cause expression of the library protein. As outlined below, the libraries can be the basis of a variety of display techniques, including, but not limited to, phage and other viral display technologies, yeast, bacterial, and mammalian display technologies. The conditions appropriate for library protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction.

As will be appreciated by those in the art, the type of cells used for displaying a library in the present invention can vary widely. Basically, a wide variety of appropriate cells can be used, including yeast, bacteria, archaebacteria, fungi, and insect and animal cells, including mammalian cells. In various embodiments, the display library may be displayed on, but is not limited to, *Drosophila melanogaster* cells, *Saccharomyces cerevisiae* and other yeasts, *E. coli*, *Bacillus subtilis*, SF9 cells, C129 cells, 293 cells, *Neurospora*, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells.

Yeast Display

In one embodiment, library protein is produced in yeast cells. Yeast expression systems are well known in the art, and include expression vectors for *Saccharomyces cerevisiae*, *Schizosaccharomyces pombe*, *Candida albicans*, *Hansenula polymorpha*, *Kluyveromyces lactis*, *Kluyveromyces fragilis*, *Ustilago maydis*, *Pichia pastoris*, *Pichia methanolica*, *Pichia guillermondii* and *Candida maltosa*.

Exemplary vectors include, but are not limited to, YIp-based vectors (integrating plasmids), such as YIp5, YRp vectors (replicating plasmids with an autonomously replicating sequence (ARS)), such as YRp17, YEp vectors (episomal plasmids with a 2 micron element) such as YEp13 and YCp vectors (plasmids with an ARS and a centromeric element), such as YCp19. Other examples of the YEp vectors include YEp24, YEp51, and YEp52, which are cloning and expression vehicles useful in the introduction of genetic constructs including expression cassettes into yeast cells. An additional vector format includes yeast artificial chromosomes (YACs).

In various embodiments, the expression cassettes comprise a promoter (e.g., a heterologous promoter) operably linked to a polynucleotide encoding a display molecule. Suitable promoters for expression of display molecules in yeast include the promoters for metallothionein, 3-phosphoglycerate kinase, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EP073,657. Other suitable promoters for expression in yeast include the promoters from GAL1 (galactose), PGK (phosphoglycerate kinase), ADH (alcohol dehydrogenase), AOX1 (alcohol oxidase), HIS4 (histidinol dehydrogenase), and the like. Still other promoters, which have the additional advantage of transcription controlled by growth conditions, are the promoter regions for alcohol dehydrogenase 2, isocytochrone C, acid phosphatase, degradative enzymes associated with nitrogen metabolism, and the afore-mentioned metallothioncin and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

In some embodiments, the yeast expression vector also includes a selectable marker gene to allow for the selection of yeast strains that have been transformed. Suitable selection genes include genes which render the bacteria resistant to drugs such as kanamycin, puromycin, methotrexate, hygromycin B, nourseothricin, and bialaphos. Other suitable selection markers include, but are not limited to, genes that permit growth in auxotrophic conditions such as TRP1 for tryptophan auxotrophs, URA3 or uracil auxotrophs, LEU2 for leucine auxotrophs, HIS3 for histidine auxotrophs, LYS2 for lysine auxotrophs, and MET15 for methionine auxotrophs.

Mammalian Display

In one embodiment, the library proteins are expressed in mammalian cells. Mammalian cells include, but are not limited to, mouse, rat, chicken, pig, horse, cow, primate and human cells, although as will be appreciated by those in the art, that any prokaryotic or eukaryotic cell can be used. Accordingly, suitable mammalian cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as, by way of non-limiting examples, hemopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc.

Mammalian expression systems are also known in the art, and include, by way of non-limiting examples, retroviral and lentiviral systems. A mammalian promoter is any DNA sequence capable of binding mammalian RNA polymerase and initiating the downstream (3') transcription of a coding sequence for library protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. In some embodiments, the promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived from SV40.

Bacterial Display

In one embodiment, library proteins are expressed in bacterial systems. Bacterial expression systems are well known in the art. A suitable bacterial promoter is any nucleic acid sequence capable of binding bacterial RNA polymerase and initiating the downstream (3') transcription of the coding sequence of library protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence that is 3-9 nucleotides in length located 3-11 nucleotides upstream of the initiation codon.

The expression vector may also include a signal peptide sequence that provides for secretion of the library protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

Display Molecules

Library proteins may be displayed on a cell surface through fusion to cell-wall polypeptides or binding partners. Fusion proteins comprising a library protein or peptide and complexes comprising a library protein or peptide are collectively referred to herein as display molecules.

In one embodiment, a display molecule is made as a fusion protein, using techniques well known in the art. Proteins are commonly displayed on the surface of yeast through either N-terminal or C-terminal linkage to the yeast protein Aga2p, which forms a covalent bond with the yeast cell-wall protein Aga1. Therefore, in one embodiment, the library protein or peptide may be fused to a cell-wall polypeptide, or a binding partner thereof, for the purpose of surface display. In one embodiment, a protein is fused to a long amino acid stalk that serves to tether the protein to the surface of a cell in an Aga2p-independent manner, for instance, using a pYDS series vector (as described in application WO2016077249A1).

In one embodiment, the library protein may be made as a fusion protein to increase expression, stability, or for other reasons. Fusion partners which may be used include, but are not limited to, targeting sequences which allow the localization of the library members into a subcellular or extracellular compartment of the cell, rescue sequences or purification tags which allow the purification or isolation of either the library protein or the nucleic acids encoding them; stability sequences, which confer stability or protection from degradation to the library protein or the nucleic acid encoding it, for example resistance to proteolytic degradation, or combinations of these, as well as linker sequences as needed.

Suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signaling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, cell wall and cellular membrane; and b) extracellular locations via a secretory signal. In one embodiment, localization is to a subcellular location or to the outside of the cell via secretion.

In one embodiment, the library member comprises a rescue sequence. A rescue sequence is a sequence which may be used to purify or isolate either the candidate agent or the nucleic acid encoding it. Thus, for example, peptide rescue sequences include purification sequences such as the His6 tag for use with Ni affinity columns and epitope tags for detection, immunoprecipitation or FACS (fluoroscence-activated cell sorting). Suitable epitope tags include myc, the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the expression construct, via PCR, related techniques, or hybridization.

In one embodiment, the library nucleic acids, proteins or peptides of the invention are labeled. By "labeled" herein is meant that nucleic acids, proteins or peptides of the invention have at least one element, isotope or chemical compound attached to enable the detection of the nucleic acids, proteins or peptides. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In one embodiment, the library protein is purified or isolated after expression. Library proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the library protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the library protein. In some embodiments, no purification will be necessary.

Antibody Display

The skilled artisan would appreciate, based upon the disclosure provided herein, that the display molecule of the invention may include an antibody, a fragment thereof, or a mimetic thereof. In one embodiment, a library of display molecules comprises a population of cells wherein each cell displays a single antibody, fragment thereof, or mimetic thereof recognizing a single antigenic epitope. In various embodiments, the antibody or antibody mimetic may be a polyclonal antibody, a monoclonal antibody, a chimeric antibody, a humanized antibody, a single chain antibody, a nanobody, an affibody, an anticalin, a monobody, or any combination thereof.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide.

Nucleic acid encoding a monoclonal antibody may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., (supra) and in the references cited therein, and in Gu et al. (1997, Thrombosis and Hematocyst 77:755-759), and other methods of humanizing antibodies well-known in the art or to be developed.

The present invention also includes the use of humanized antibodies. The humanized antibodies of the invention have a human framework and have one or more complementarity determining regions (CDRs) from an antibody, typically a mouse antibody. When the antibody used in the invention is humanized, the antibody may be generated as described in Queen, et al. (U.S. Pat. No. 6,180,370), Wright et al., (supra) and in the references cited therein, or in Gu et al. (supra). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least about 70%, or at least about 80%, or at least about 90%, or at least about 95%, or at least about 96%, or at least about 97%, or at least about 98%, or at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Antibody mimetics (or mimics) include organic compounds that, like antibodies, can specifically bind antigens, but that are not structurally related to antibodies. Antibody mimetics may be small molecules, nucleic acid molecules, or artificial peptides or proteins. Exemplary antibody mimetics that may be displayed in a display library of the invention include, but are not limited to, affibody molecules, affilins, affimers, affitins, alphabodies, anticalins, avimers, DARPins, fynomers, kunitz domain peptides, nanobodies and monobodies.

Exemplary nanobodies include, but are not limited to, nanobodies comprising the amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10, or fragments, or variants thereof. In one embodiment, a nanobody of the invention comprises at least 20, 30, 40, 50, 60, 70, 80, 90, or more than 100 amino acid residues of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10. In one embodiment, a nanobody of the invention comprises an amino acid sequence with at least 70%, at least about 80%, at least about 90%, at least about 95%, at least about 96%, at least about 97%, at least about 98%, or at least 99% identity (or any integer in between 70 and 99) to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10.

Methods for Library Preparation

The invention provides methods for preparing a display library using several techniques including, but not limited to, fragmenting one or more nucleic acid molecules, digesting one or more nucleic acid molecules, purifying one or more nucleic acid molecules, PCR amplification of one or more nucleic acid molecules and ligating one or more nucleic acid molecules to one or more yeast expression vectors of the invention.

In one embodiment, the invention includes generation of display libraries in a high-throughput manner. In one embodiment, a high throughput method of generating the display library of the invention includes performing the steps of the reaction in 96-well or 384-well plate format. In one embodiment, one or more of nucleic acid size verification steps and purification steps may be included or optionally omitted to facilitate high-throughput display library construction.

In one embodiment, a method for generating a display library includes the steps of isolating mRNA from a cell, generating cDNA therefrom and ligating the cDNA into a vector for expression in and display on the surface of a yeast cell. Many methods of purifying nucleic acid molecules are known in the art. In one embodiment, a method for purifying a nucleic acid molecule is phenol/chloroform extraction. In one embodiment, the method for purifying a nucleic acid molecule is column based. In one embodiment, the method for purifying a nucleic acid molecule is bead based. In one embodiment, the method for purifying a nucleic acid molecule is ethanol precipitation. In one embodiment, multiple methods of purification of nucleic acid molecules can be performed at different steps during the preparation of a display library of the invention. In one embodiment, the selection of a purification method is determined by the quantity or concentration of nucleic acid to be purified.

Multiple nucleic acid size verification steps are possible during the construction of the display library of the invention. In one embodiment, nucleic acid size verification steps are performed using gel electrophoresis. In one embodiment, size verification steps are performed using a low-melting point agarose. In one embodiment, size verification is performed using a capillary gel electrophoresis system. In one embodiment size verification is performed using a Bioanalyzer.

There are also multiple appropriate methods for performing one or more size selection steps during display library preparation. In one embodiment, a method for nucleic acid size selection is gel extraction of an appropriate band. In one embodiment, a method of size selection is bead based. In one embodiment, a method of size selection includes contacting multiple nucleic acid molecules with an amount of suspended size selection beads. In one embodiment, beads appropriate for size selection include AMPure XP beads.

In certain embodiments, the method comprises ligation of one or more input DNA into a yeast expression vector. For example, vectors, including but not limited to the vectors described elsewhere herein, may be ligated to an isolated DNA molecule.

Transformation of Cells for Expression of a Display Library

Individual expression vectors may be transiently transformed into a cell, maintained stably as an episomal plasmid or artificial chromosome, or stably integrated into a cell to generate a strain displaying a protein of interest. Methods of introducing exogenous nucleic acid into prokaryotic and eukaryotic cells, are well known in the art, and will vary with the cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells can be selected by phenotype determined by a selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media.

In general, a plurality of display molecules is transformed into a plurality of cells to generate a display library, wherein generally each cell within the library contains a member of the library, i.e. a different library member, although as will be appreciated by those in the art, some cells within the library may not contain a library member and some may contain a duplicate member.

Microbes

In one embodiment, the library nucleic acids are introduced into a first plurality of cells, and the ability of a second plurality of cells, different from the first plurality of cells, i.e., generally a different cell type, is screened for interaction with the library expressing cells. Thus, in one embodiment, the methods of the present invention comprise introducing a molecular library of library members into a plurality of cells, to generate a cellular display library. The display library is then contacted with a second plurality of cells and screened for a desired phenotype. In one embodiment, a desired phenotype is binding of one or more of the second population of cells to a library display cell.

In one embodiment, the second population of cells are microbial cells. Microbial cells suitable for use in the methods of the invention include gram positive bacteria and gram-negative bacteria, as well as archaebacteria.

In one embodiment, the second population of cells comprises at least one cell from at least one commensal microbe. Exemplary commensal microbes include, but are not limited to, *peptostreptococcus* spp., *clostridium* spp., *lactobacillus* spp. (*Lactobacillus acidophilus, Lactobacillus crispatus, Lactobacillusj ohnsonii, Lactobacillus sakei, Lactobacillus bulgaris, Lactobacillus jensenii, Lactobacillus rhamonsus, Lactobacillus reuteri, Lactobacillus casei* var *rhamnosus, Lactobacillus gasseri, Lactobacillus fermentum, Lactobacillus iners, Lactobacillus helveticus, Lactobacillus leichmannii, Lactobacillus brevis, Lactobacillus plantarum, Lactobacillus delbrueckii, Lactobacillus vaginalis, Lactobacillus salivarius, Lactobacillus coleohominis, Lactobacillus pentosus, propionibacerium* spp., *eubacterium* spp., *bifidobacterium* spp., *prevotella* spp., *bacteroides* spp., *fusobacterium* spp., *veillonella* spp., *diphtheroides* spp., and *actinomycetales* spp.

In one embodiment, the second population of cells comprises at least one cell from at least one pathogenic microbe. Exemplary pathogenic microbes include, but are not limited to, *Staphylococcus aureus, Staphylococcus epidermidis*, Group B *streptococcus* spp., *Enterococcus faecalis* spp., *staphylococcus* spp., *Actinomyces israelii, Actinomyces neuii, Escherichia coli, klebsiella* spp., *proteus* spp., *Enterobacter* spp., *Acinetobacter* spp., *citrobacter* spp. and *pseudomonas* spp.

In one embodiment, the second population of cells comprises at least one cell from at least one potentially pathogenic commensal microbe (i.e., pathobiont). Exemplary pathobionts include, but are not limited to, *helicobacter* spp., segmented filamentous bacteria, pathogenic *Bacteroides fragilis* strains, pathogenic *Enterobacter* spp., pathogenic *Prevotellaceae* spp., pathogenic *Erysipelotrichaceae* spp., and pathogenic *Clostridia* spp.

In one embodiment, the second population of cells comprises at least one cell from a single microbial species, strain, or isolate. In one embodiment, the second population of cells comprises at least two cell from multiple microbial species, strains, or isolates. In one embodiment, the second population of cells comprises at least one cell from at least 1, 2, 3, 4, 5, 6, 7, 8, 9, 10, 15, 20, 25, 30, 35, 40, 45, 50 or more than 50 microbial species, strains, or isolates.

In one embodiment, the second population of cells are labeled. For example, in one embodiment, the cells have been transformed to carry an expression vector for expression of a fluorescent protein (e.g., GFP, etc.).

Screening Methods

Screening of a second population of cells using the display library of the invention may be done using standard techniques. The display library cells may be grown in or on one media, and then combined with a second plurality of cells, and the effect measured. In one embodiment, there may be direct contact between the cells, permitting binding between a display molecule of the first population and a member of the second population.

In one embodiment, the library display cells are treated to conditions suitable for the expression of the library members (for example, when inducible promoters are used), to produce the library proteins.

In one embodiment, the screening method comprises screening a library of multiple display molecules against a single microbial organism. Such an embodiment is useful, for example, in identifying one or more host proteins, antibodies, antibody mimetics, or amino acid sequences that are bound by a single microbial organism. In such an embodiment, it may be beneficial for the microbe to further comprise a marker for selection or isolation of a bound display molecule:microbe complex. For example, in one embodiment, the microbe is labeled with biotin to allow for selection of a bound display molecule:microbe complex using streptavidin beads. In another embodiment, the microbe is labeled with a fluorescent dye such as CFSE to permit selection of a bound display molecule:microbe complex using FACs sorting. Other distinguishable labels or markers include fluorescent dyes that bind to nucleic acids such as the SYTO dyes (Thermo Scientific), antibodies or other affinity reagents that bind components of the microbial cell wall or membrane such as anti-LPS, or a genetically encoded marker such as a fluorescent protein (e.g., green fluorescent protein) or a surface-expressed epitope such as an affinity tag.

In one embodiment, the screening method comprises screening a population of cells displaying a single display molecule against a mixed population of microbial organisms. Such an embodiment is useful, for example, in identifying one or more microbes that can be bound by a specific display molecule. In such an embodiment, it may be beneficial for the display molecule or the cell comprising a display molecule to further comprise a marker for selection or isolation of a bound display molecule:microbe complex. For example, in one embodiment, the display molecule is conjugated to biotin to allow for selection of a bound display molecule:microbe complex using streptavidin beads.

In one embodiment, one or more rounds of selection can be used to purify a bound display molecule:microbe complex. A round of selection can comprise a positive selection, a negative selection, a counter-selection, or any combination thereof. In various embodiments, the screening method comprises at least 1, 2, 3, 4, 5, or more than 5 rounds of selection. In one embodiment, the screening method comprises both a positive selection and a negative selection. Exemplary selection methods that may be used in the screening method of the invention include, but are not limited to the use of MACs, FACs, streptavidin beads, and magnetic beads.

Following purification of a display molecule:microbe complex, a bound display molecule or microbe can be detected using any appropriate method known in the art. For example, in one embodiment, one or more nucleic acid sequence encoding one or more display molecule can be isolated from the cell and sequenced. In one embodiment, the 16S rRNA gene can be amplified from one or more bound microbes from a mixed population of microbes and sequenced to identify the one or more bound microbes that interacts with a display molecule. In one embodiment, total DNA can be isolated from one or more bound microbes from a mixed population of microbes and sequenced (i.e., whole genome or metagenomic sequencing) to identify the one or more bound microbes that interacts with a display molecule. In one embodiment, one or more nucleic acid sequences encoding the display molecules or nucleic acid sequences isolated from microbes are sequenced using an high-throughput sequencing method (e.g., using an Illumina based Hi-Seq, or Mi-Seq or Life Technologies PGM based sequencing platform.) In one embodiment, one or more nucleic acid sequences encoding the display molecules or nucleic acid sequences isolated from microbes are sequenced using Sanger sequencing.

Identifying Therapeutic Targets

In one embodiment, the BASEHIT screen, such as can be performed using the display libraries described herein, identifies a molecule, such as a protein or peptide, that mediates a host-microbe interaction. Such a molecule (e.g., protein or peptide, etc.) and the encoding nucleic acid sequence may then serve as a target for modulating host-microbe interaction in the host organism.

In one embodiment, an identified target can serve as a target for therapeutic or pharmaceutical development. In one embodiment, the target for therapeutic or pharmaceutical development may be the protein, mRNA, or DNA or an activator or inhibitor of an identified target.

Assaying Therapeutic Agents

In one embodiment, the BASEHIT methodology of the invention can be used to assay candidate agents for binding to library members for an effect on host-microbial interaction. By "candidate agent" or "candidate drugs" or grammatical equivalents herein is meant any molecule, e.g., proteins (which herein includes proteins, polypeptides, and peptides), small organic or inorganic molecules, polysaccharides, polynucleotides, antibodies, antibody mimetics etc. which are to be tested in the BASEHIT method of the invention. Candidate agents encompass numerous chemical classes. In one embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, including those with at least two of the functional chemical groups. The candidate agents often comprise cyclical carbon or heterocyclic structures and/or aromatic or polyaromatic structures substituted with one or more chemical functional groups.

Candidate agents can be obtained from a wide variety of sources, as will be appreciated by those in the art, including synthetic or natural compounds, or known libraries. As will be appreciated by those in the art, the present invention provides a method to determine the effect of a candidate agent on host-microbe interaction comprising performing the BASEHIT assay in the presence of one or more candidate agents.

In one embodiment, candidate agents are synthetic compounds. Any number of techniques are available for the random and directed synthesis of a wide variety of organic compounds and biomolecules, including expression of randomized oligonucleotides. In one embodiment, candidate agents are natural compounds (e.g., a secreted or extracted protein from a bacteria, fungus, plant or animal).

In one embodiment, a candidate agent comprises an antibody or antibody fragment. In one embodiment, the candidate agent comprises a bispecific antibody targeting both a microbe and a display molecule. The candidate agent can be assayed, for example through performing the BASEHIT assay in the presence of one or more bispecific antibodies to identify those antibodies that are able to facilitate interaction of a microbe with a display molecule. Exemplary bispecific antibodies that can be developed using the BASEHIT method include antibodies targeting a microbe and further targeting a display molecule comprising an antibody, antibody fragment or antibody mimetic. In one embodiment, a bispecific antibody targets an IgG, IgA, IgM, or IgE. Such an embodiment is useful, for example, in targeting antibodies to a microbe of interest.

Therapeutic Agents

In one embodiment, the methods of the invention are useful for identifying a therapeutic agent for use in mediating host:microbe interactions. Therefore, in various embodiments, the invention relates to compositions comprising therapeutic agents identified using the methods described herein and their use in treating or preventing a disease or disorder associated with a microbe.

In one embodiment, the method of identifying a therapeutic agent that mediates host:microbe interaction comprises performing the BASEHIT assay in the presence of one or more candidate agent and evaluating the effect of the agent on the ability of at least one microbe to interact with at least one display molecule. In one embodiment, the therapeutic agent is one that increases or promotes interaction of a microbe with a display molecule. In one embodiment, the interaction is increased by at least 2%, 3%, 4%, 5%, 6%, 7%, 8%, 9%, 10%, 20%, 30%, 40%, 50%, 75%, 100%, or greater than 100% compared to a control value. In one embodiment, the therapeutic agent is one that decreases or inhibits interaction of a microbe with a display molecule. In one embodiment, the interaction is decreased by at least 2%, 3%, 4%, 5%, 6%, 7%, 8%, 9%, 10%, 20%, 30%, 40%, 50%, 75%, 100%, or greater than 100% compared to a control value.

In one embodiment, the present invention relates to a composition comprising a therapeutic agent that interacts with a microbe. For example, in some aspects, the BASEHIT assay can identify peptides that bind to a microbe, where the identified peptide can then be used in the development of a therapeutic agent targeting the microbe. In some embodiments, the identified peptides are used in the development of affinity reagents, including but not limited to, nanobodies, conventional antibodies, affibodies, anticalins, and monobodies.

In one embodiment, an affinity reagent is a nanobody comprising an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 or SEQ ID NO:10, or fragments, or variants thereof.

In one embodiment, the composition comprises an antibody or fragment thereof. In some embodiments, the antibody or fragment thereof is useful for therapeutic applications. For example, in some embodiments, the antibody or fragment thereof, derived from the BASEHIT assay described herein, can be used to reduce or eliminate pathogenic bacteria, or inhibit bacterial pathogenicity. In some embodiments, the antibody or fragment thereof, is modified to produce precision antibiotics that specifically target a bacteria of interest. For example, in some embodiments, the antibody or fragment thereof is fused to an antibiotic, bacteriolysin, bacteriocin, or other compound that results in the reduction of the pathogenicity of a pathogenic bacteria. For example, in one embodiment, the composition comprises an antibody or fragment thereof fused, linked, or otherwise attached to a delivery vehicle comprising an antibiotic or other agent that reduces the pathogenicity of a pathogenic bacteria. In some embodiments, the antibody or fragment thereof is fused to an agent that promotes the growth of beneficial bacteria. For example, the antibody or fragment thereof can be fused to specific growth-promoting nutrients. In one embodiment, the composition comprises an antibody or fragment thereof fused, linked, or otherwise attached to a delivery vehicle comprising a growth-promoting agent.

In one embodiment, the therapeutic agent comprises a bispecific antibody targeting both a microbe and a display molecule. Exemplary bispecific antibodies that can be developed using the BASEHIT method include antibodies targeting a microbe and further targeting a display molecule comprising an antibody, antibody fragment or antibody mimetic. In one embodiment, a bispecific antibody targets an IgG, IgA, IgM, or IgE antibody. Such an embodiment is useful, for example, in targeting antibodies to a microbe of interest.

In one embodiment, the bispecific antibody comprises a region that binds to a specific microbe, as derived from the BASEHIT method described herein. In one embodiment, the bispecific antibody further comprise a region that binds to luminal IgA.

In some embodiments, the composition comprises a diagnostic agent comprising an affinity reagent described herein, including, but not limited to nanobodies, conventional antibodies, affibodies, anticalins, and monobodies. In some embodiments, the diagnostic agent comprises an antibody or fragment thereof, that specifically binds a bacteria of interest to determine the presence or abundance of a particular bacterial species that is associated with disease or that protects from disease.

In one embodiment, the invention relates to methods of treatment or prevention of a disease or disorder associated with a microbe using the therapeutic agents of the invention. Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art Kits The present invention also pertains to kits useful in the methods of the invention. Such kits comprise various combinations of components useful in any of the methods described elsewhere herein. For example, in one embodiment, the kit comprises components useful for performing BASEHIT screens as described herein. In one embodiment, the kit contains a cellular display library. In one embodiment, the kit contains a library of expression vectors to be used in generating a cellular display library. In one embodiment, the kit contains additional components. In one embodiment, an additional component includes but is not limited to instructional material. In one embodiment, instructional material for use with a kit of the invention may be provided electronically.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: The BASEHIT Approach for Identifying Proteins Involved in Host Microbe Interaction Studies of invasive pathogens have indicated that a small number of host proteins may serve as receptors for a variety of bacterial species (Kochut and Dersch, 2013, Eur J Pharm Biopharm, 84(2):242-250). If similar trends are observed in the microbiota—that is, a small number of surface or secreted host proteins react promiscuously with a variety of microbes that mediate a common effect on the host—those host proteins may present compelling therapeutic targets for modulation of intestinal immunity regardless of the microbial community present.

A yeast-display based system has been developed to profile protein-microbe interactions in high throughput. This strategy, referred to herein as BASEHIT (BActerial Selection for Elucidation of Host-microbe Interactions in high Throughput), uses the well-established technology of yeast surface display (Boder and Wittrup, 1997, Nat Biotechnol, 15(6):553-557; Gai and Wittrup, 2007, Curr Opin Struct Biol, 17(4):467-473) combined with selection with intact microbes to identify proteins that bind to specific microbes. An experimental overview of BASEHIT is shown in FIG. 1.

Yeast surface display is a technique heavily used for antibody discovery and protein engineering (Gai and Wittrup, 2007, Curr Opin Struct Biol, 17(4):467-473; Feldhaus et al., 2003, Nat Biotechnol, 21(2):163-170), wherein a library of proteins of interest (e.g. antibody fragments or protein receptor variants) can be displayed on the surface of yeast and selected for binding activity towards a ligand of interest. In this way, proteins with binding activity for a target of interest can be identified from large libraries in excess of $10^9$ variants (Feldhaus et al., 2003, Nat Biotechnol, 21(2):163-170). Proteins are commonly displayed on the surface of yeast through either N-terminal or C-terminal linkage to the yeast protein Aga2p, which forms a covalent bond with the yeast cell-wall protein Aga1 (Boder and Wittrup, 1997, Nat Biotechnol, 15(6):553-557; Wang et al., 2005, Protein Eng Des Sel, 18(7):337-343). This allows for the display of proteins in multiple formats, as some proteins fold properly only in the presence of a free amino or carboxy terminus (Wang et al., 2005, Protein Eng Des Sel, 18(7): 337-343; Weiskopf et al., 2013, Science, 341(6141): p. 88-91). Proteins are then selected with ligands of interest conjugated to a marker that can be used for MACS or FACS—common conjugates include biotin (for streptavidin-based selections) or fluorescent dyes (for FACS sorting).

The ability of yeast displaying a variety of proteins to be selected using intact microbial cells, rather than recombinant protein ligands, was assessed to identify proteins that interact with the microbe of interest. To test this, Fc region of the human IgG1 protein N297Q (aglycosylated) mutant was displayed on the surface of yeast tethered to a long glycosylated stalk of 649 amino acids in the pYDS649HM vector (as described in WO2016077249A1) that serves to anchor the protein to the cell wall in an Aga2p-independent manner. Yeast displaying the Fc fragment co-expressed EGFP from the same bidirectional promoter. Upon selection with cell-surface biotinylated *Staphylococcus aureus* (which expresses Protein A that binds with high affinity to IgG1 Fc) and enrichment using magnetic streptavidin-coated beads, about a 30-fold enrichment of GFP+ yeast was observed in a single round of selection, demonstrating the possibility of using intact microbes as selection reagents for yeast display (FIG. 4A).

Figure 2A:
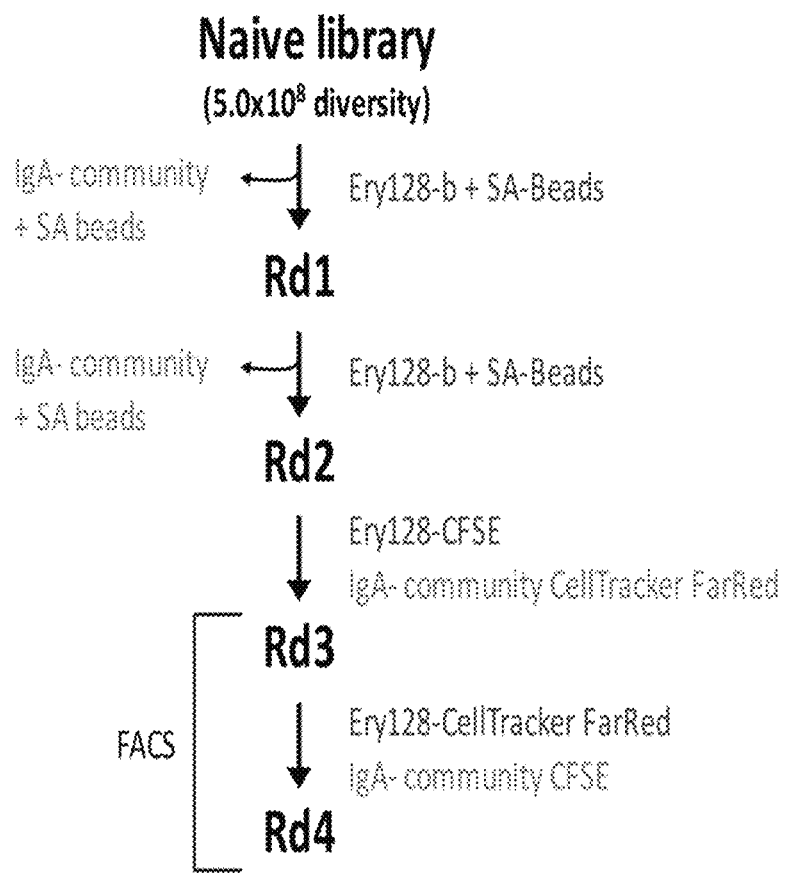
FIG. 2A through FIG. 2B, depicts exemplary experimental addition selection details for *Erysipelotrichaceae* 128 (Ery128) nanobodies.
Figure 2B:
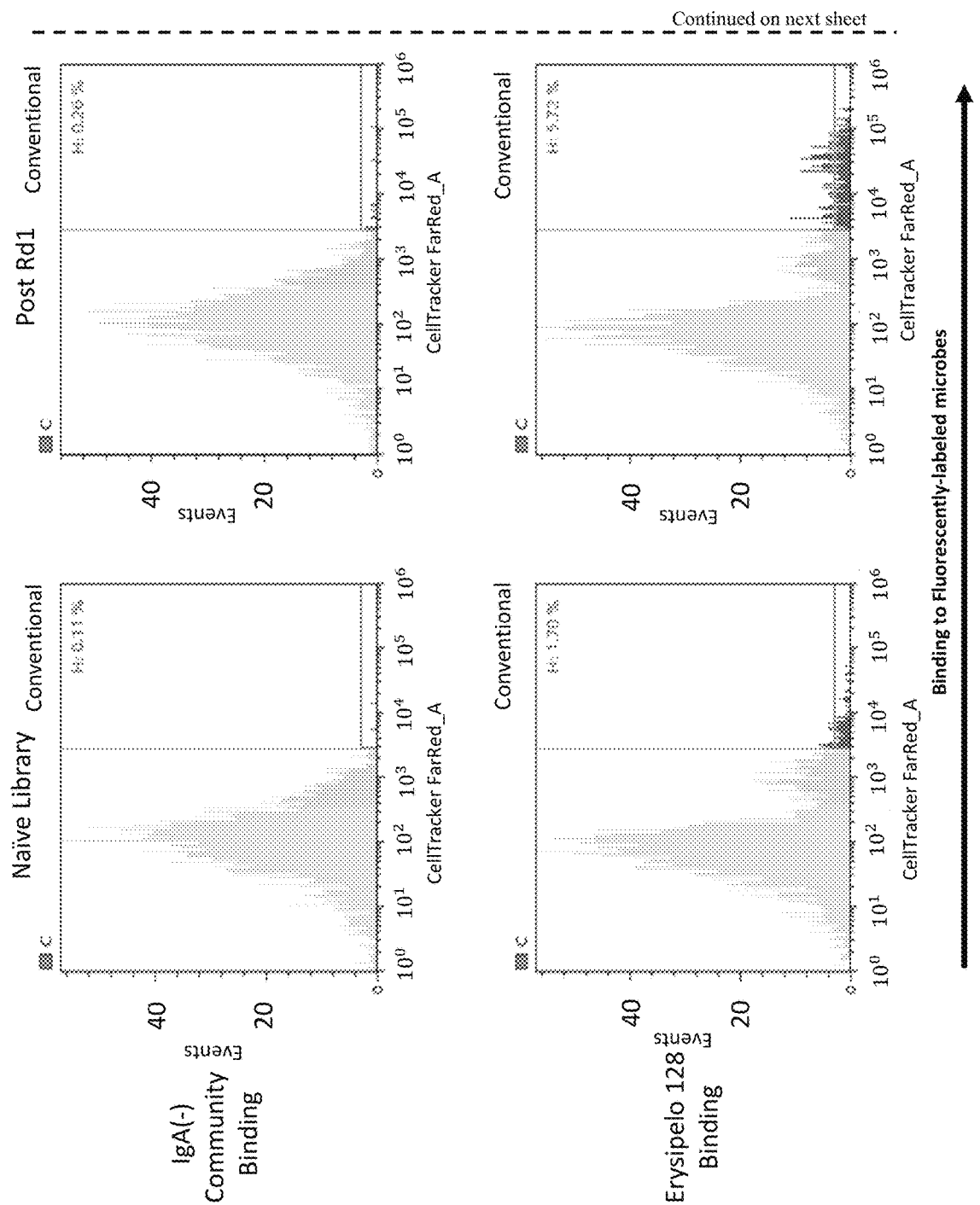
Figure 3:
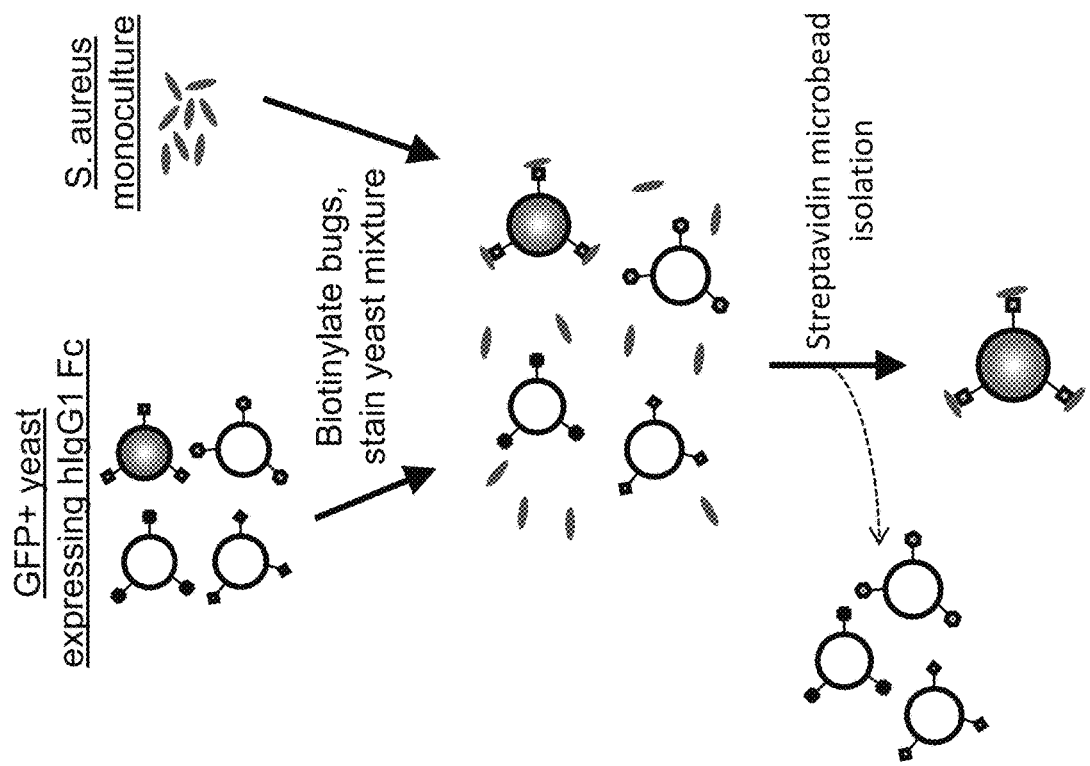
FIG. 3 depicts a schematic diagram of validation of the selection results with known microbe-protein interaction: *S. aureus* interaction with hIgG1 Fc.
Figure 4B:
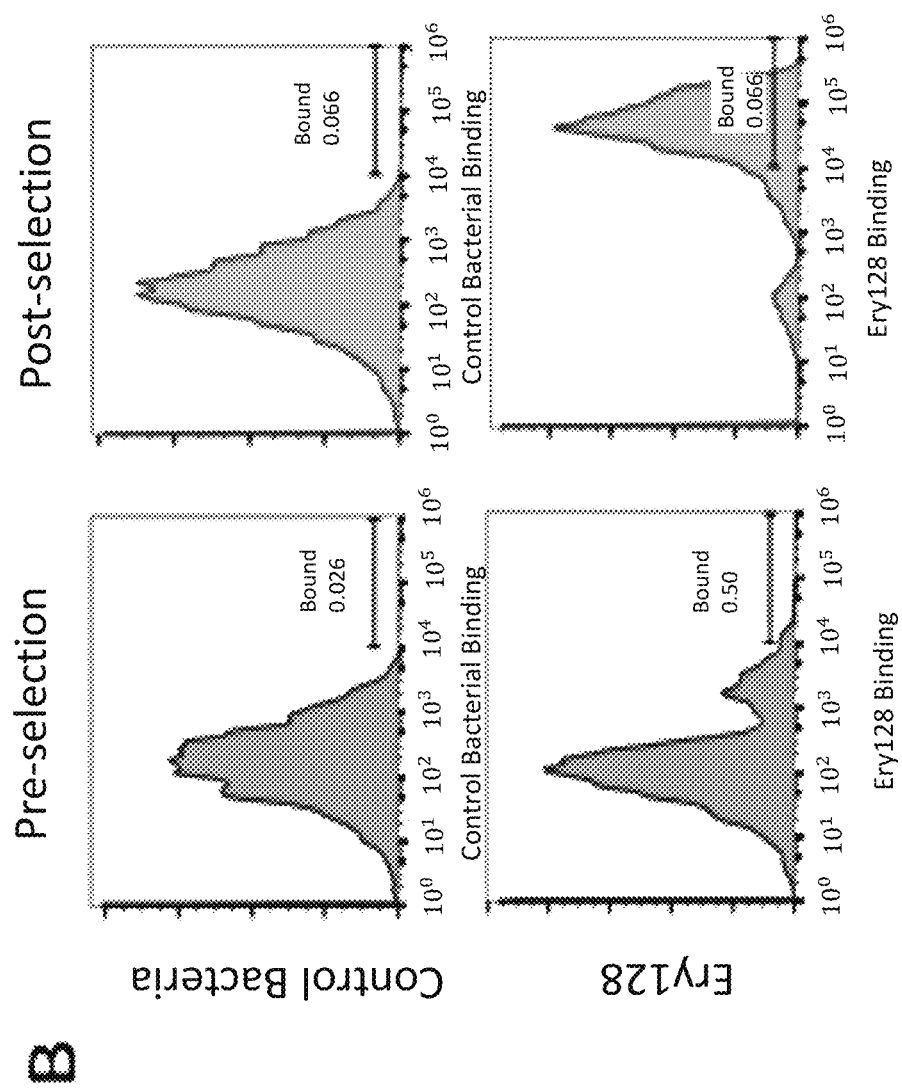
Figure 4C:
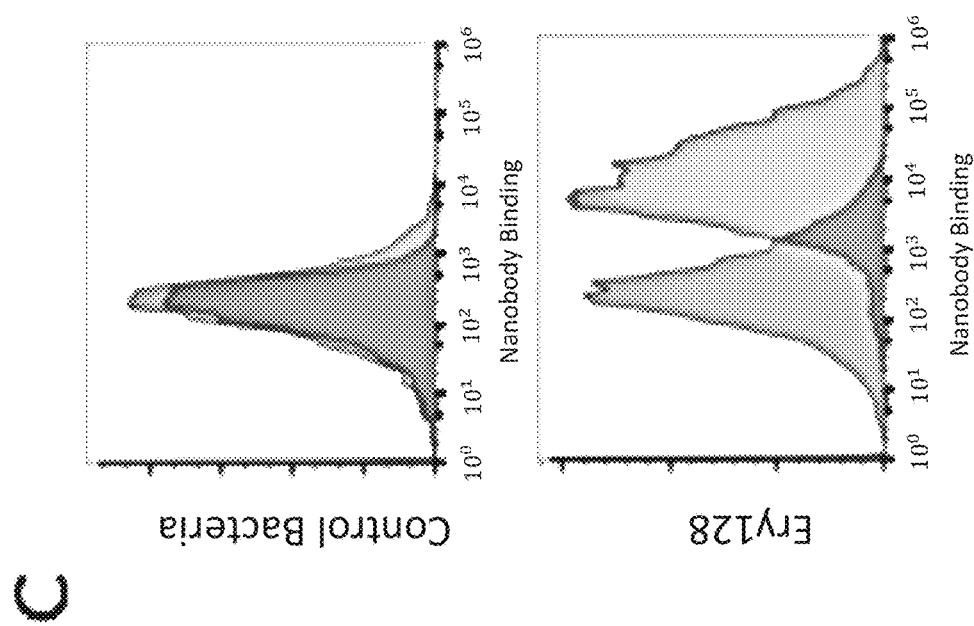
Figure 4D:
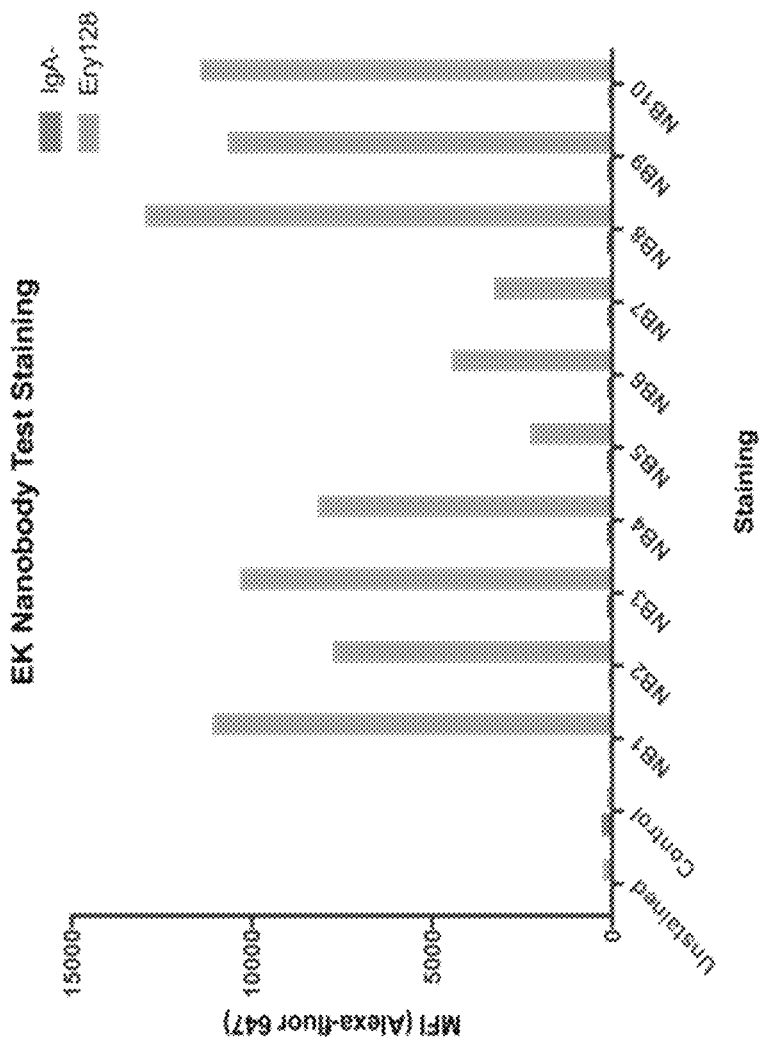
Figures 6A, 6B, 6C:
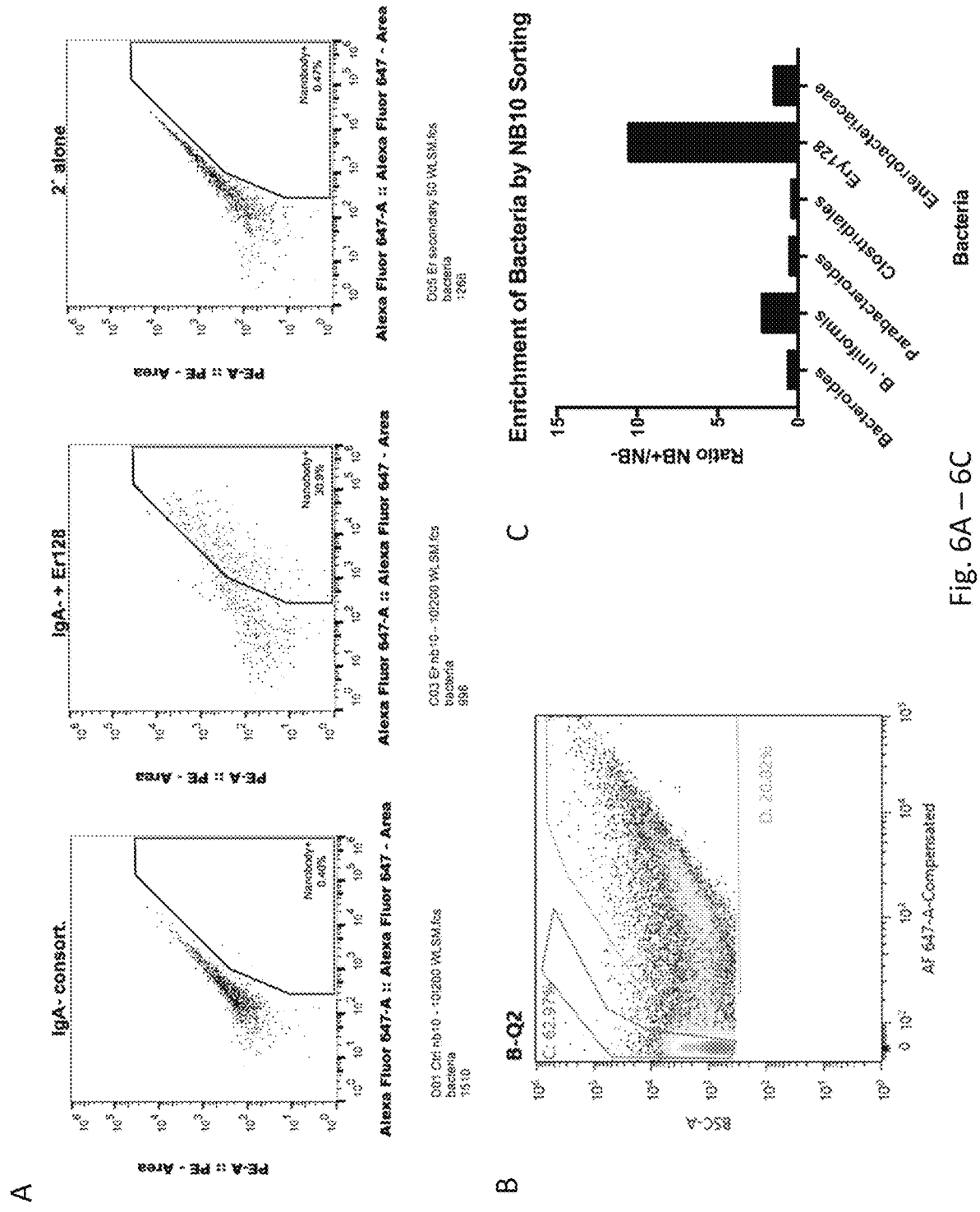
FIG. 6A through FIG. 6C, depicts an exemplary use of one Ery128 nanobody to demonstrate specificity and utility of novel proteins isolated through the BASEHIT technique.

To validate that this process could be used on large libraries, a yeast library containing $5*10^8$ single-domain antibody-like molecules was screened (nanobodies, Muyldermans, 2013, Annu Rev Biochem, 82(1):775-97) using a novel colitogenic microbe *Erysipelotrichaceae* sp. (Palm et al., 2014, Cell, 158(5):1000-1010). For this selection, cell-surface biotinylation of monocultured *Erysipelotrichaceae* and magnetic streptavidin-coated beads was used to perform MACS separations of the yeast library in initial rounds, and CFSE labeling of the microbes was used to perform FACS separations in the final rounds (FIG. 2). In between selections, counter-selection was used to remove clones that bound a consortium of "immunologically inert" microbes (IgA-community, Palm et al., 2014, Cell, 158(5):1000-1010), to ensure that the nanobodies would recognize unique features of *Erysipelotrichaceae* rather than general bacterial features such as cell wall or membrane components. The results were validated using *S. aureus* interaction with hIgG1 Fc (FIG. 3, FIG. 4A). After four rounds of MACS and FACS selection, there was greatly enriched binding of the yeast pool towards *Erysipelotrichaceae*, but no increase in binding of the IgA-community (FIG. 4B). The oligoclonal yeast pool contained 10 unique nanobodies, which were cloned into vectors for mammalian expression (FIG. 5). All nanobodies stained *Erysipelotrichaceae* specifically when prepared recombinantly (FIGS. 4C and 4D). One nanobody, Nb10, was further validated by staining of fecal bacteria from mice colonized with the IgA-community or the IgA-community together with Ely128, and sorting of nanobody-bound bacteria followed by 16s rRNA sequencing. Nb10 specifically recognized bacteria in the feces of mice colonized by Ery128 (FIGS. 4A and 4B), and sorted nanobody-positive bacteria were highly enriched for Ery128 by 16s rRNA sequencing (FIG. 4C). These experiments have established BASEHIT as a valid platform for discovering proteins that interact with microbes of interest, derived both from host proteins as well as from libraries of affinity reagents.

Example 2: 'Conventional' BASEHIT

Figure 8:
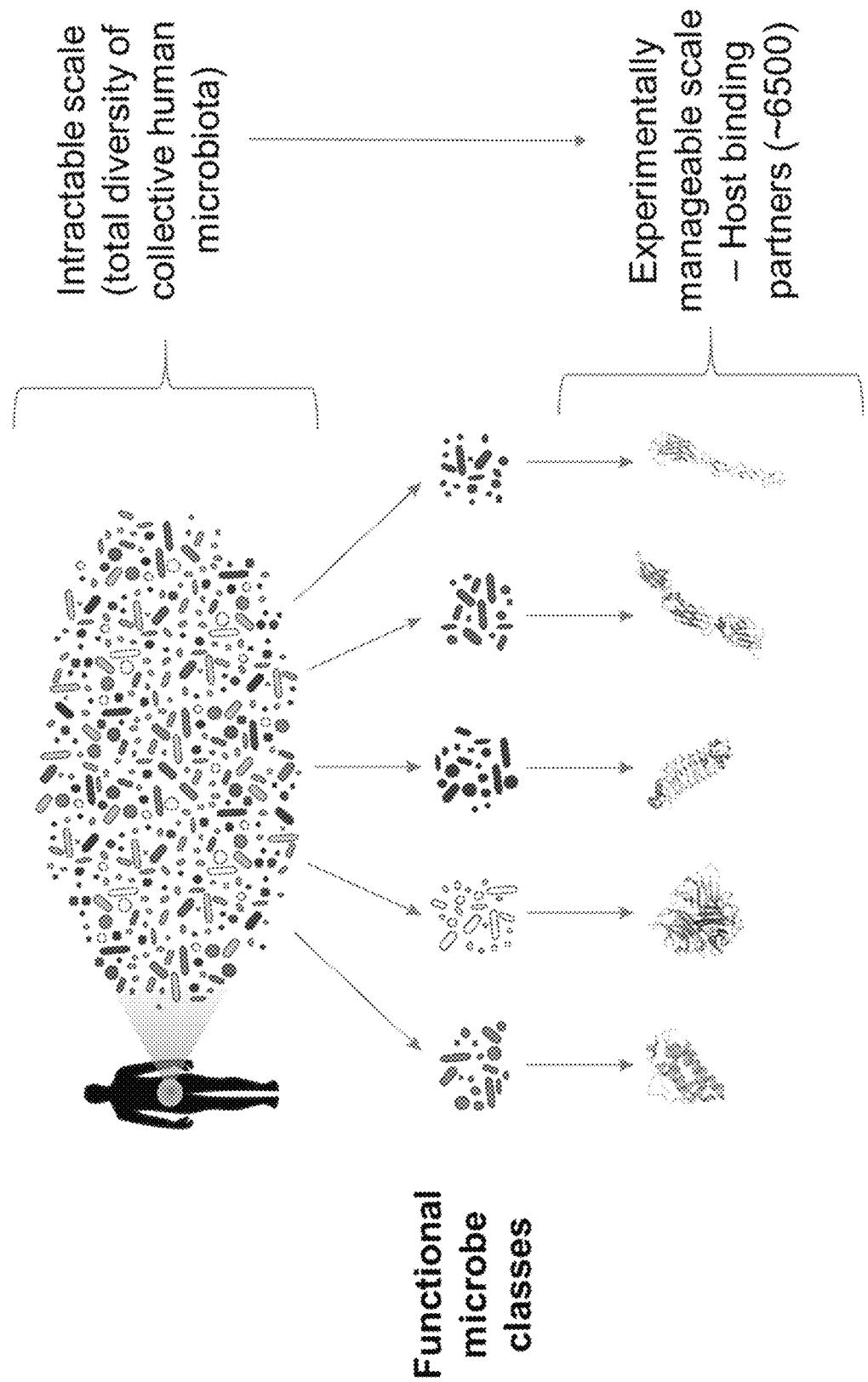
FIG. 8 depicts a schematic diagram showing that BASE-HIT is useful for classifying gut microbes by host binding partners.
Figure 9:
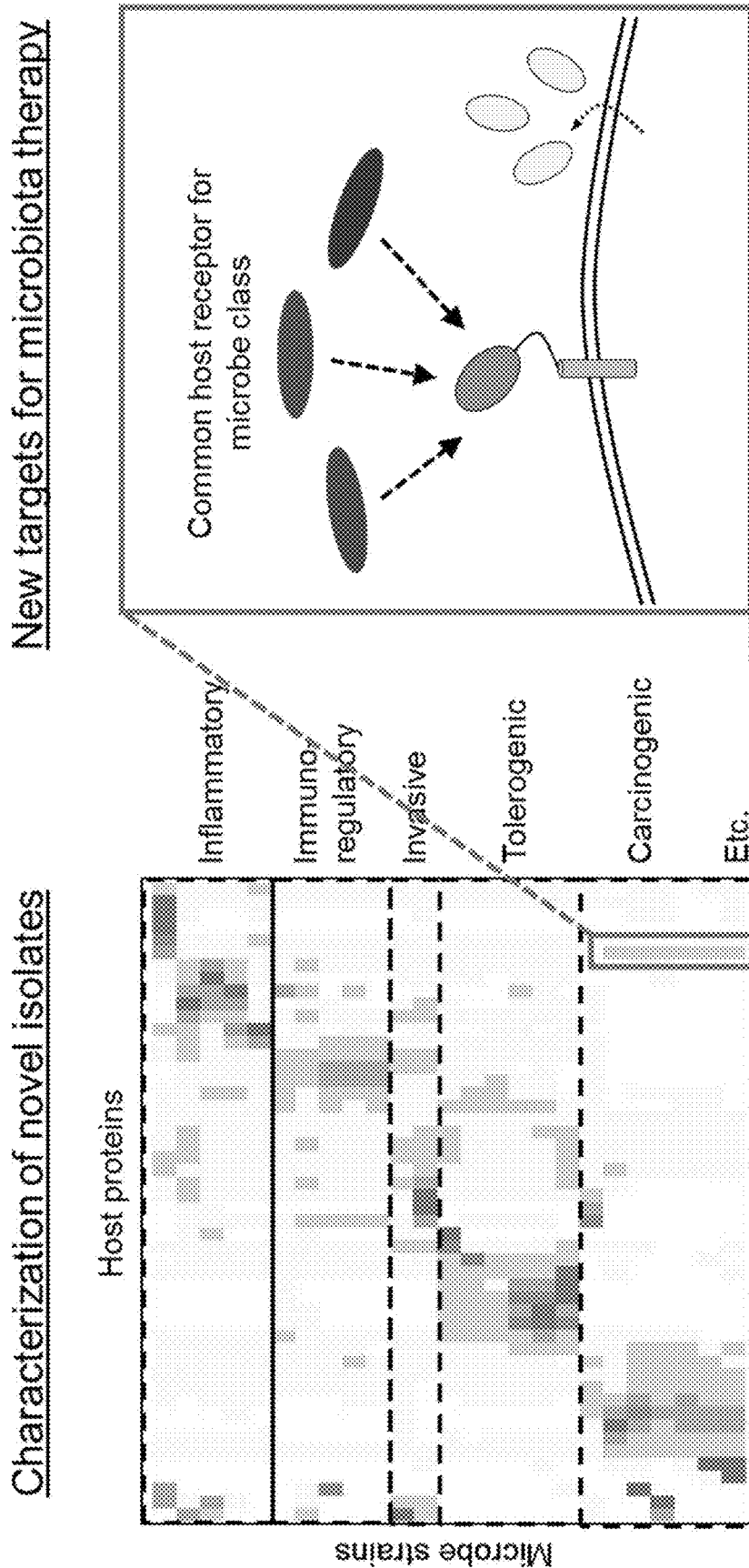
FIG. 9 depicts a schematic diagram showing that BASE-HIT is useful for identifying new therapeutic targets.

One application of BASEHIT is in the discovery of host-proteins involved in host-microbe interactions of various forms—e.g., host-pathogen interactions, as well as detrimental and/or beneficial interactions between the host and its microbiota (FIG. 8). BASEHIT can be used to identify common host pathways rather than rare microbial strains These proteins are ideal targets for therapeutic intervention (FIG. 9) since they can be targeted via conventional pharmacological and biological approaches.

Figure 7:
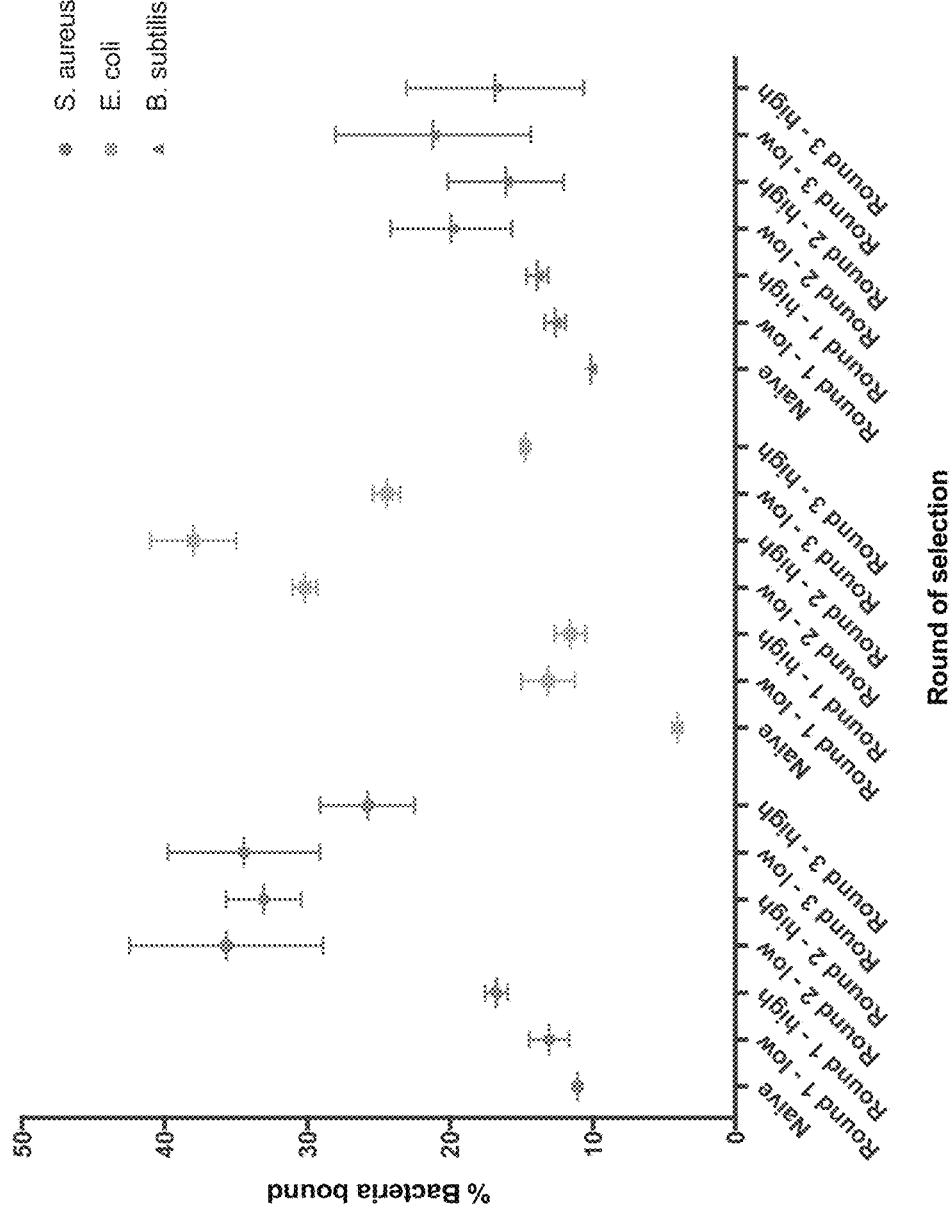
FIG. 7 depicts exemplary experimental results demonstrating BASEHIT proof-of-principle to detect host proteins binding specific microbes. A library containing >1000 human extracellular and secreted proteins was enriched for binding to multiple bacterial species (*E. coli, S. aureus, B. subtilis*) by successive rounds of MACS, using two different amounts of bacteria ("high" and "low"). The percentage of the library that bound each species at each round is represented.

To demonstrate that BASEHIT may be used to select host proteins that bind microbes of interest, a proof-of-principle experiment was performed with 3 bacterial species (*E. coli, S. aureus, B. subtilis*) selected on a library containing >1000 human extracellular and secreted proteins on the surface of yeast (FIG. 7). The yeast library was stained with two different ratios of cell-surface biotinylated bacterial cells to yeast cells ("high" and "low") and bound yeast were selected by MACS. Three rounds of MACS selection were performed, and at the end, all yeast were stained with the respective bacterial species and the percentage of the library that bound the bacteria was detected with fluorescent streptavidin. All selections increased the percentage of the library that bound the bacteria (relative to the "naïve" unselected library), with increased rounds of selection tending to improve enrichment. This experiment validates that host proteins that recognize a particular bacterial species may be enriched through BASEHIT for multiple species.

Example 3: Antibody BASEHIT

Antibody BASEHIT enables the rapid and reliable production of microbe-specific affinity reagents (including nanobodies, conventional antibodies, affibodies, anticalins, monobodies, etc.) in a matter of weeks. Such highly-specific affinity reagents open the door to the development of myriad potential therapeutic or diagnostic agents.

First, antibodies specific for bacterial entities involved in bacterial pathogenicity (e.g., adhesion proteins, toxins, secretion systems) are potentially therapeutically useful in and of themselves since they may directly block pathogenicity. Second, bacterial-specific antibodies can be modified to impart specific activities of therapeutic utility. For example, antibodies may be modified to produce precision antibiotics that will eliminate a given microbe without disrupting beneficial microbes colonizing the same environment. This could be achieved in multiple ways: e.g., fusing antibodies with bacteriolysins (e.g., bacteriocins), using antibodies to retarget bacteriophages, or for precise delivery of nanoparticles containing traditional antibiotics. On the other hand, bacterial specific antibodies could also be used to promote the growth of beneficial species, for example by specifically delivering growth-promoting nutrients in nanoparticles.

Bacterial-specific antibodies may be useful therapeutics in and of themselves. In particular, formatting to mucosal isotypes (including IgM, IgA1 and IgA2) may facilitate precision manipulation of microbiota composition at barrier surfaces, including the skin, gastrointestinal tract, and urogenital tract. In addition, fusions with other antibody isotypes (e.g., IgG) could be used as targeted antibiotics in vivo at non-barrier surfaces.

Another application of BASEHIT would be the creation of a new class of bispecific antibodies/antibody fragments that retarget existing antibodies (including IgG, IgA, IgM, and IgE) to a specific microbial species. One embodiment of this approach is in creation of a bispecific agent where one arm targeted an antigen expressed on a disease-causing intestinal microbe and the other arm targeted luminal IgA. In effect, this reagent would effectively repurpose the existing IgA repertoire in a microbe-specific fashion without the need for the initiation of a new immune response (e.g., by vaccination). For example, a bi-specific anti-*C. difficile* antibody that also bound IgA could be given prophylactically to at-risk patients to prevent *C. difficile* outgrowth and potential sequale such as colitis. Another embodiment would be to administer a bispecific anti-Ery128/anti-IgA antibody to patients with Ery128-induced colitis in order to restrict Ery128 growth and/or pathogenicity.

In addition to their utility as therapeutics, bacterial specific antibodies could also be useful in the generation of diagnostics. For example, bacterial specific antibodies could be used to determine whether an individual harbors a particular bacterial species or strain that is associated with or protects from disease.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of detecting molecules involved in microbial interactions, the method comprising the steps of:
    a) contacting a first population of cells comprising one or more display molecules with a second population of cells comprising cells from at least one microbial species, wherein the one or more display molecule comprises a nanobody comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10;
    b) selecting at least one bound display molecule:microbe complex; and
    c) detecting the identity of at least one of a bound display molecule.

2. The method of claim 1, wherein the first population of cells comprises a population of yeast cells.

3. The method of claim 1, wherein the at least one display molecule comprises a library of host protein sequences.

4. The method of claim 1, wherein the microbial species is selected from the group consisting of a commensal microbe of the host species and a pathogenic microbe of the host species.

5. The method of claim 1, further comprising identifying the at least one bound display molecule as a therapeutic target.

6. A method of detecting a microbe that can interact with at least one target sequence, the method comprising the steps of:
    a) contacting a first population of cells comprising at least one display molecule comprising at least one target sequence, with a second population of cells comprising cells from at least one microbial species, wherein the one or more display molecule comprises a nanobody comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10;
    b) selecting at least one bound display molecule:microbe complex; and
    c) detecting the identity of the at least one bound microbe.

7. The method of claim 6, wherein the first population of cells comprises a population of yeast cells.

8. The method of claim 6, wherein the at least one target sequence comprises a host protein sequence.

9. The method of claim 6, wherein the at least one microbial species is selected from the group consisting of a commensal microbe of the host species, and a pathogenic microbe of the host species.

* * * * *